US012629083B2

(12) United States Patent
Bar-Tal et al.

(10) Patent No.: US 12,629,083 B2
(45) Date of Patent: May 19, 2026

(54) CARDIAC MAPPING VIA NEAR-FIELD IDENTIFICATION FROM PHYSIOLOGICAL SIGNALS

(71) Applicant: Biosense Webster (Israel) Ltd., Yokneam (IL)

(72) Inventors: Meir Bar-Tal, Haifa (IL); Richard P.M. Houben, Lanaken (BE); Lior Botzer, Timrat (IL); Milad El Haddad, Helsinki (FI)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 113 days.

(21) Appl. No.: 17/539,384

(22) Filed: Dec. 1, 2021

(65) Prior Publication Data

US 2022/0192576 A1 Jun. 23, 2022

Related U.S. Application Data

(60) Provisional application No. 63/129,326, filed on Dec. 22, 2020.

(51) Int. Cl.
| | |
|---|---|
| *A61B 5/367* | (2021.01) |
| *A61B 5/00* | (2006.01) |
| *A61B 5/283* | (2021.01) |
| *A61B 5/287* | (2021.01) |
| *A61B 5/363* | (2021.01) |
| *A61B 18/12* | (2006.01) |
| *A61B 18/14* | (2006.01) |

(52) U.S. Cl.
CPC .............. *A61B 5/367* (2021.01); *A61B 5/283* (2021.01); *A61B 5/7203* (2013.01); *A61B*

*5/287* (2021.01); *A61B 5/363* (2021.01); *A61B 2018/1253* (2013.01); *A61B 18/1492* (2013.01)

(58) Field of Classification Search
CPC ...................... A61B 5/367; A61B 2017/00053
See application file for complete search history.

(56) References Cited

U.S. PATENT DOCUMENTS

| | | | |
|---|---|---|---|
| 5,391,199 | A | 2/1995 | Ben-Haim |
| 5,443,489 | A | 8/1995 | Ben-Haim |
| 5,558,091 | A | 9/1996 | Acker et al. |
| 5,944,022 | A | 8/1999 | Nardella et al. |
| 5,983,126 | A | 11/1999 | Wittkampf |

(Continued)

OTHER PUBLICATIONS

Castells et al., "Principal Component Analysis in ECG Signal Processing," 2007, Eurasip J. Advances in Signal Processing, pp. 1-21. (Year: 2007).*

(Continued)

*Primary Examiner* — Joseph A Stoklosa
(74) *Attorney, Agent, or Firm* — Volpe Koenig

(57) ABSTRACT

A medical system is provided. The medical system includes a processing device communicatively coupled to a probe. The processing device operates to cause the medical system receive physiological signals from electrodes of the probe and decompose the physiological signals into near-field component and far-field component by using mutual information from a set of the electrodes. The processing device operates to cause the medical system utilize the near-field components for localizing in time where a wave went under at least one of the plurality of electrodes.

20 Claims, 12 Drawing Sheets

(56) References Cited

U.S. PATENT DOCUMENTS

| | | | |
|---|---|---|---|
| 6,172,499 B1 | 1/2001 | Ashe | |
| 6,177,792 B1 | 1/2001 | Govari et al. | |
| 6,266,551 B1 | 7/2001 | Osadchy et al. | |
| 6,456,864 B1 | 9/2002 | Swanson et al. | |
| 6,690,963 B2 | 2/2004 | Ben-Haim et al. | |
| 6,788,967 B2 | 9/2004 | Ben-Haim et al. | |
| 10,321,837 B2 | 6/2019 | Shilemay et al. | |
| 2009/0093806 A1 | 4/2009 | Govari et al. | |
| 2009/0138007 A1 | 5/2009 | Govari et al. | |
| 2012/0071730 A1* | 3/2012 | Romero | A61B 5/361 |
| | | | 600/509 |
| 2012/0184863 A1 | 7/2012 | Harlev et al. | |
| 2013/0253504 A1* | 9/2013 | Fang | A61B 5/4848 |
| | | | 606/41 |
| 2014/0081114 A1 | 3/2014 | Shachar et al. | |
| 2014/0187991 A1* | 7/2014 | Thakur | A61N 1/056 |
| | | | 600/509 |
| 2014/0200575 A1* | 7/2014 | Spector | A61B 5/316 |
| | | | 606/40 |
| 2015/0238102 A1 | 8/2015 | Rubinstein et al. | |
| 2015/0342536 A1* | 12/2015 | Kovtun | A61B 5/0245 |
| | | | 600/509 |
| 2016/0310030 A1 | 10/2016 | Yellin | |
| 2017/0065198 A1 | 3/2017 | Ruppersberg | |
| 2019/0223744 A1 | 7/2019 | Cheng et al. | |
| 2019/0239810 A1 | 8/2019 | Solis et al. | |
| 2020/0323456 A1 | 10/2020 | Nguyen et al. | |
| 2021/0338137 A1* | 11/2021 | García Quintanilla | |
| | | | A61B 5/361 |

OTHER PUBLICATIONS

Extended European Search Report dated May 20, 2022 for European Patent Application No. 21216554.2.
Communication pursuant to Article 94(3) EPC dated Jan. 3, 2025 for European Patent Application No. 21216554.2.

* cited by examiner

CARDIAC MAPPING VIA NEAR-FIELD IDENTIFICATION FROM PHYSIOLOGICAL SIGNALS

CROSS REFERENCE TO RELATED APPLICATIONS

This application claims priority from U.S. Provisional Patent Application No. 63/129,326, entitled "VT IMPROVEMENTS ANNOTATION IMPROVEMENTS," filed on Dec. 22, 2020, which is hereby incorporated by reference as if set forth in full in this application for all purposes.

FIELD OF INVENTION

The systems and methods herein relate generally to presentation of signal processing. More particularly, the systems and methods herein provide improved cardiac mapping via near-field identification from physiological signals.

BACKGROUND

Cardiac mapping is a detailed three-dimensional map of a heart that is generated to enable medical professionals (e.g., physicians) to determine the precise location of the source of an arrhythmia. Medical professionals use these mapped images of the heart when performing procedures, such as a cardiac ablation to treat atrial fibrillation, the most common type of arrhythmia.

Generally, a three-dimensional map of the heart is created when the physician guides a catheter through the blood vessels of a patient until the catheter is inside the heart. The catheter senses electrical activity, and computer algorithms guide cardiac analyzing the electrical activity. However, these computer algorithms are often are not suited for analyzing ventricle activity (either left or right ventricle), and thus, would require additional annotation to be useful for ventricle mappings. In addition, these computer algorithms are sensitive to far-field interference. What is needed is a system and method for extracting and analyzing electrical activity while reducing interference from a far-field that, for example, would improve ventricle mapping.

SUMMARY

According to one or more embodiments, a medical system is provided. The medical system includes a processing device communicatively coupled to one or more probes. The processing device operates to cause the medical system perform receiving physiological signals from a plurality of electrodes of the one or more probes; decomposing the physiological signals into near-field component and far-field component by using mutual information from a set of the plurality of electrodes; and utilizing the near-field components for localizing in time where a wave went under at least one of the plurality of electrodes.

According to one or more embodiments, a method is provided. The method is implemented by a processing device communicatively coupled to one or more probes. The method includes receiving physiological signals from a plurality of electrodes of the one or more probes; decomposing the physiological signals into near-field component and far-field component by using mutual information from a set of the plurality of electrodes; and utilizing the near-field components for localizing in time where a wave went under at least one of the plurality of electrodes.

According to one or more embodiments, the medical system and/or the method herein are not limiting and can be embodied in one or more of an apparatus, a device, an environment, computer program produce, etc.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Figure 1:
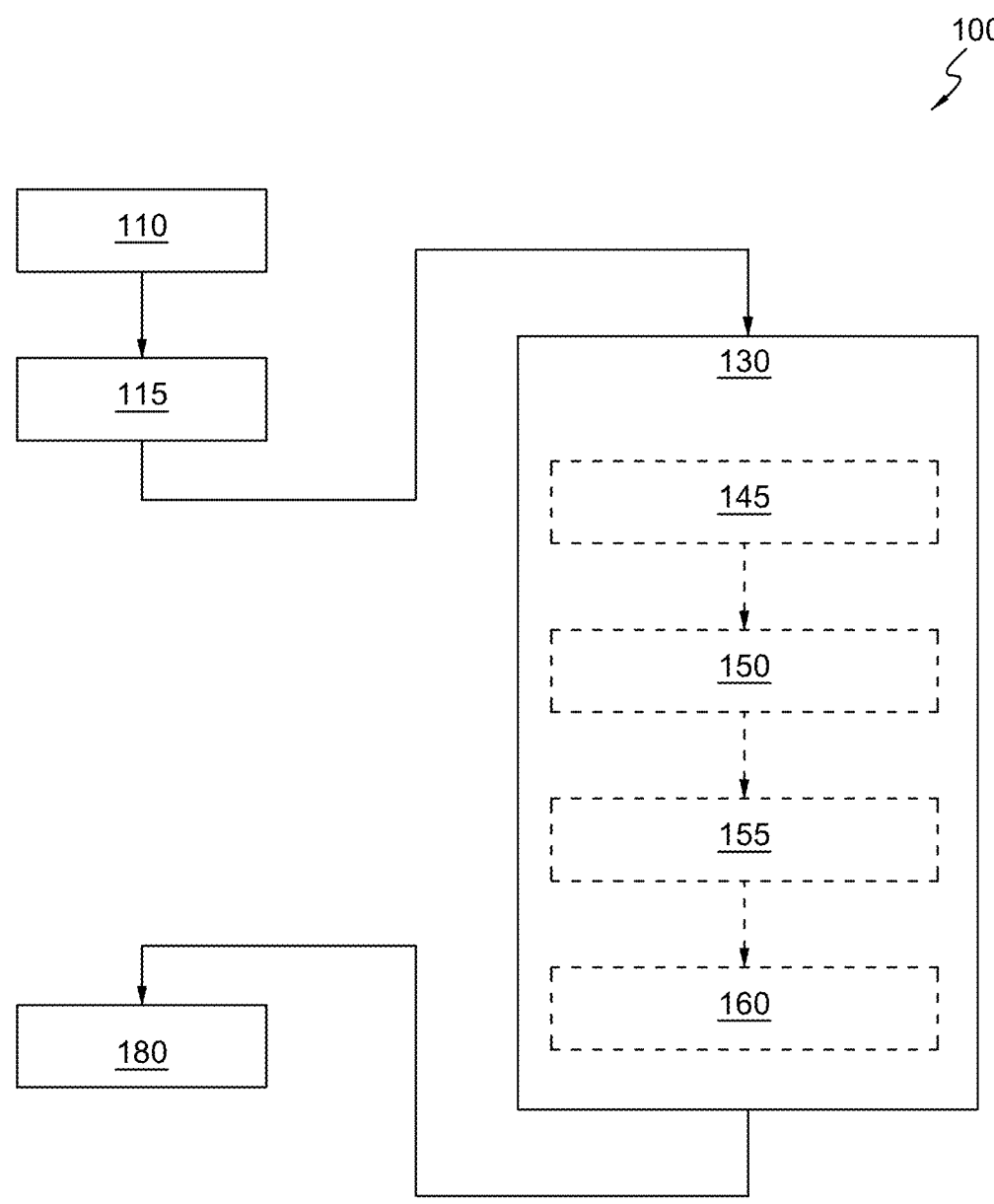
FIG. 1 depicts an exemplary method according to one or more embodiments.

The systems and methods herein relate generally to presentation of signal processing. More particularly, the systems and methods herein provide improved cardiac mapping via near-field identification from physiological signals.

Generally, cardiac arrhythmias persist as common and dangerous medical ailments, especially in aging populations. In patients with normal sinus rhythm, the heart (which is comprised of atrial, ventricular, and excitatory conduction tissue) is electrically excited to beat in a synchronous, patterned fashion. In patients with cardiac arrhythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, for example, in the region of the sino-atrial (SA) node, along the conduction pathways of the atrioventricular (AV) node and the Bundle of His, or in the cardiac muscle tissue forming the walls of the ventricular and atrial cardiac chambers.

Further, cardiac arrhythmias, including atrial arrhythmias, may be of a multiwavelet reentrant type, characterized by multiple asynchronous loops of electrical impulses that are scattered about the atrial chamber and are often self-propagating. Alternatively, or in addition to the multiwavelet reentrant type, cardiac arrhythmias may also have a focal origin, such as when an isolated region of tissue in an atrium fires autonomously in a rapid, repetitive fashion. Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

A catheter ablation-based treatment may include mapping the electrical properties of heart tissue, especially the endocardium and the heart volume, and selectively ablating cardiac tissue by application of energy. Cardiac mapping, for example, creates a map of electrical potentials (a voltage map) of the wave propagation along the heart tissue or a map of arrival times (a local time activation (LAT) map) to various tissue located points, which may be used for detecting local heart tissue dysfunction. Ablations, such as those based on cardiac mapping, can cease or modify the propagation of unwanted electrical signals from one portion of the heart to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which the ablation is to be performed.

As noted herein, through cardiac mapping, detailed three-dimensional maps of a heart are generated to enable medical professionals to determine the precise location of the source of an arrhythmia and to perform procedures, such as a cardiac ablation to treat atrial fibrillation. According to one or more embodiments, three-dimensional heart maps can be created when the medical professional guides a catheter through the blood vessels of a patient until the catheter is inside the heart. The catheter senses electrical activity and provides physiological signals that can be used to map out three-dimensional computer model of the heart. The images may be color coded to show different regions of the heart and electrical activity therein. Eventually, the heart's entire electrical activity can be completely mapped out and the medical professional can determine exactly where the abnormal electrical signals causing the heart arrhythmia are originating and can proceed with the proper treatment to eliminate the abnormal electrical activity.

The system and method herein provides a mapping engine (i.e., software stored on a memory and executable by one or more processors). The mapping engine can include one or more computer algorithms guiding cardiac mapping and ablation procedures. In contrast to conventional algorithms, such as Wavefront, LPM (Late Potential Mapping), Coherence in Ventricle, Ripple in Ventricle, and Ripple in Atrial, the mapping engine is configured to analyze ventricle activity (either left or right ventricle), as well as other activity of the heart. Thus, according to one or more technical effects, advantages, and benefits, the mapping engine reduces far-field interference (i.e., is not sensitive to far-field interference) and does not require additional annotation to be useful for ventricle mappings (i.e., provides complete mappings).

According to one or more embodiments, the mapping engine receives physiological signals from a plurality of electrodes of the one or more probes; decomposes the physiological signals into near-field component and far-field component by using mutual information from a set of the plurality of electrodes; and utilizes the near-field components for localizing in time where a wave went under at least one of the plurality of electrodes. In this regard, the mapping engine can generate one or more signal values localizing in time the near-field components and provide the one or more signal values as inputs to one or more algorithms or for a visualization. Further, the mapping engine can generate one or more signal values localizing in time the near-field components and provide the one or more signal values to a display device for a visualization.

According to one or more embodiments, the mapping engine improves annotating ventricle activity by utilizing an annotation algorithm to extract additional signals while reducing the interference from the far-field. The additional annotations can utilize to improve conventional algorithms as well. For instance, the mapping engine can present a filtered signals (beyond the annotation). In addition, the mapping engine can utilize a catheter having multiple unipolar measuring electrodes to conclude what is mutual/common and what is local activity. Note that mutual/common activity (e.g., mutual information) sensed by each electrode can be considered far-field components or electrical activity occurring throughout a heart chamber that are commonly received. Further, far-field components or electrical activity can be qualified based on their origination away from the electrode, which can be at distances on an order of centimeters. Note that local activity sensed by each electrode can be considered near-field components or electrical activity directly detected by each electrode. Further, near-field components or electrical activity can be qualified based on their origination close to the electrode, which can be at distances on an order of millimeters. In some cases, far-field components are identified by their relatively large amplitudes compared to near-field components of relatively small amplitudes. According to one or more embodiments, the identified components can be provided by the mapping engine to one or more algorithms for further analyzation and/or for a visualization.

FIG. 1 is an exemplary method 100 according to one or more embodiments. The method 300 can be embodied by the mapping engine. Generally, the method 100 is an implementation of improved cardiac mapping via near-field identification from physiological signals. In turn, the mapping engine, implementing the method 100, can present signals for interpretation that near-field components. In this way, the mapping engine provides one or more technical effects, advantages, and benefits of removing interference from a far-field to improve ventricle mapping.

The method 100 begins at block 110, one or more probes are placed with respect to cardiac tissue of a patient. The one or more probes can be placed by a medical professional. For instance, the one or more probes can be percutaneously inserted by a medical professional through the patient's vascular system into the heart of the patient.

The one or more probes can each include at least one electrode. The electrodes can be placed on the skin (i.e., that generate body surface physiological signals) and/or inside the heart using a specialized probe (i.e., that generate intracardiac physiological signals). For instance, according to one or more embodiments, a probe can be a catheter or a cardiac catheter equipped with a variety of electrode and/or sensors, such as location, electrical, pressure, image and/or temperature sensors, for the purpose of gathering information (i.e., physiological signals) for diagnostic mapping and/or delivering therapeutic treatment (e.g., performing ablation). Examples of catheters include, but are not limited to, fixed catheter, deflectable catheter, bidirectional catheter, unidirectional catheter, tricuspid mapping catheter, halo-shaped tip catheter, basket catheter, and/or lasso-shaped catheter.

Figure 2:
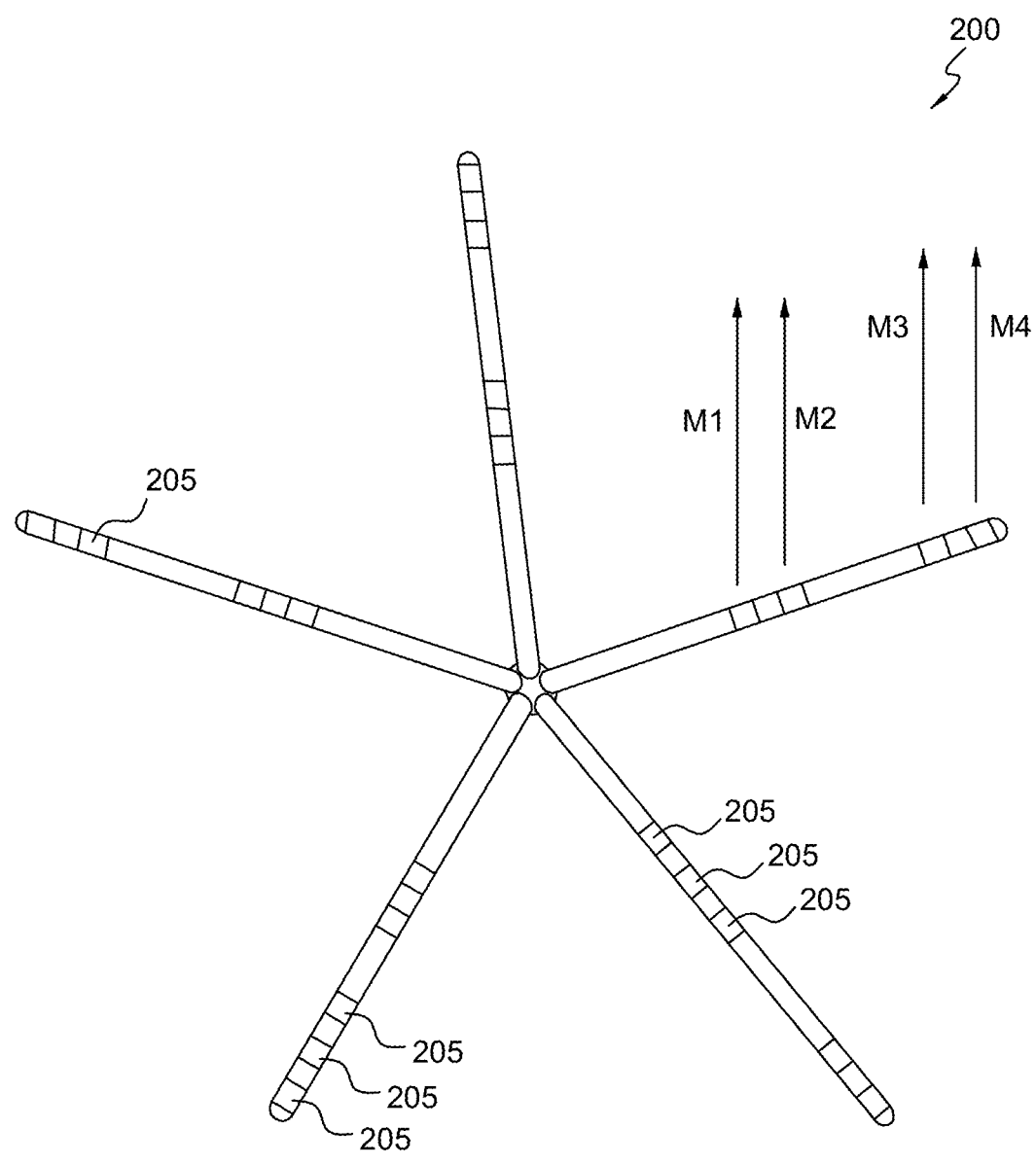
FIG. 2 depicts an exemplary catheter according to one or more embodiments.

Turning to FIG. 2, an exemplary catheter 200 is shown, which may be utilized in accordance with certain implementations according to one or more embodiments. The example catheter 200 can be a high-density mapping catheter and may include, but is not limited to include, electrodes 205 that provide one or more physiological signals (as represented by M1, M2, M3, and M4). For instance, the electrodes 205 can number at least three (3) arranged in any combination of pairs. According to one or more embodiments, the example catheter 200 can include at least five (5) arms, and in some cases eight (8) or more, and the electrodes 205 can include twenty (20) or forty-eight (48) unipolar electrodes positioned in pairs or couples 1 millimeter or 2 millimeter apart from one another (e.g., higher density improves performance). Further, the exemplary catheter 200 can be a OCTARAY™ Mapping Catheter and/or PENT-ARAY® NAV ECO High Density Mapping Catheter by Biosense Webster®.

Returning to FIG. 1, at block 115, the mapping engine receives physiological signals from a plurality of electrodes of the one or more probes. The mapping engine can be communicatively coupled to the one or more probes, to receive the physiological signals in real time or for storage.

At block 130, the mapping engine decomposes the physiological signals.

For instance, the mapping engine performs an electrocardiograph (ECG) and/or an intracardiac electrogram (ICEG) that includes decomposing the physiological signals. The ECG/ICEG are processes of decomposing/analyzing/recording electrical activity of a heart over a period of time using the physiological signals of the plurality of electrodes (e.g., with the ICEG, at least one of the electrodes is inside the heart). That is, the plurality of electrodes of the one or more probes detect and provide these signals (a.k.a., physiological signals), which the mapping engine uses to identify small electrical changes that arise from the heart muscle's electrophysiologic pattern of depolarizing during each heartbeat. The ECG/ICEG can be performed over a period of time, such as 10 seconds, for example. In this way, the overall magnitude and direction of the electrical depolarization at the heart is captured at each moment throughout the cardiac cycle. The ECG/ICEG can be recorded during a diagnostic or therapeutic procedure. The procedure duration may vary from tens of minutes to several hours. During each therapeutic procedure, usually there are several dozens of ablation sessions, each of which last several seconds up to approximately 1 minute, for example.

Thus, generally, to the medical professional, the ECG/ICEG conveys a large amount of information about a structure of a heart and a function of its electrical conduction system. That is, during each heartbeat, a healthy heart has an orderly progression of depolarization. This orderly pattern of depolarization gives rise to the characteristic ECG/ICEG tracing. And, among other things, the ECG/ICEG can be used to measure the rate and rhythm of heartbeats, the size and position of the heart chambers, the presence of any damage to the muscle cells or conduction system of the heart, the effects of cardiac drugs, and the function of implanted pacemakers. The mapping engine provides the technical effect, advantage, and benefit of signal interpretation of the ECG/ICEG in support of fundamentally understanding the electrical conduction system of the heart, as normal conduction starts and propagates in a predictable pattern, and deviation from this pattern can be a normal variation or be pathological. Note that the mapping engine can be considered an electrocardiograph, while a test by and an output of the mapping engine can be considered an electrocardiography and electrocardiogram (i.e., graph of voltage versus time), respectively. For the sake of brevity, electrocardiography, electrocardiograph, and electrocardiogram can all be referred to herein as ECG, and may also be referred to as EKG.

According to one or more embodiments, the mapping engine can identify electrical activity of the physiological signals in a form of raw ECG signal waves, as the electrical activity propagates across cardiac tissue. The near-field component is of interest to the medical professional, and to various algorithms intended to correctly identify the propagation of the activation within the tissue (Wavefront, LPM, Ripple, etc.). Thus, it is desirable to isolate/disuse/remove/discard interference from the far-field signals to improve mapping.

By way of example, the mapping engine can decompose the physiological signals into near-field and far-field components by using mutual information from a set of the plurality of electrodes. The mutual information includes far-field components of the physiological signals that equate to commonly received electrical activity by the one or more probes and occurring throughout the heart. In some cases, the far-field components can be qualified based on their origination away from the electrode, which can be at distances on an order of centimeters. Note that local activity sensed by each electrode can be considered near-field components individually and/or directly detected by each electrode. Further, the near-field components can be qualified based on their origination close to the electrode, which can be at distances on an order of millimeters. In some cases, the far-field components have large amplitudes relative to small amplitudes of near-field components.

Note that, to ascertain usable signals from the electrical conduction system of the heart, the measured signals (i.e., received physiological signals) need to be filtered to remove any unwanted and spurious signals. More particularly, at sub-block 145, the mapping engine can cancel out raw signals of the physiological signals that are morphologically different than any remaining raw signals. This cancelation can occur prior to calculating a signal projection (as further described herein with respect to FIG. 7, complexes 764.2 and 764.3).

At sub-block 150, the mapping engine utilizing remaining raw signals (i.e., multiple raw ECG signal waves) to determine the signal projection. The signal projection can include a reference signal that replicates the morphology of the far-field component. Variants on calculating the signal projection are disclosed. According to one or more embodiment, the signal projection can be an initial estimate of a signal that is intended to be morphologically as close as possible to a far-field component. By way of example, when the signal projection is developed using mean averaging, the signal projection can be referred to as an ensemble mean as described herein.

Figure 3:
FIG. 3 depicts a diagram according to one or more embodiments.
Figure 3:
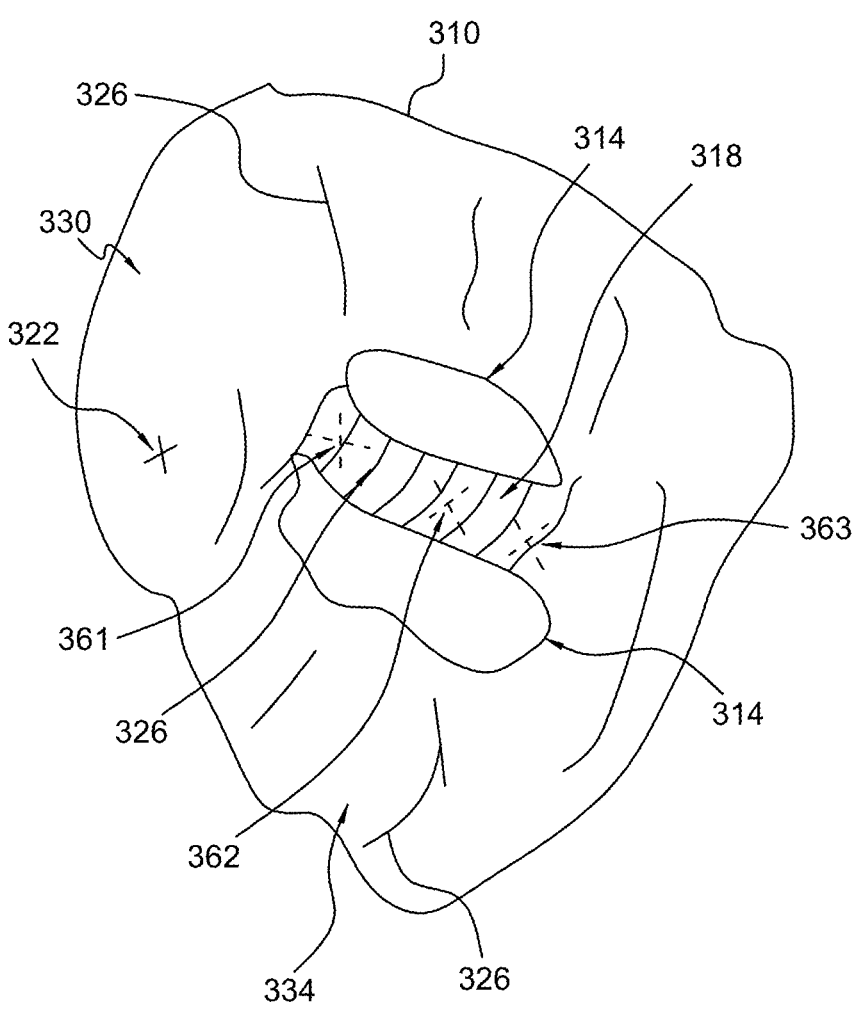

Turning to FIG. 3, a diagram 300 representing cardiac tissue and wave propagation within the heart, including areas of healthy tissue and areas of scarred or diseased tissue according to one or more embodiments. The diagram 300 particularly shows representations of ventricle activity within a heart, i.e., a segment of cardiac tissue 310 located within a ventricle (either right or left ventricle) of the heart. The segment of cardiac tissue 310 includes two areas 314 of scarred or diseased tissue demarcated by thickened lines. A narrow strip 318 of cardiac tissue is shown located between the two encircled areas of diseased tissue 314, which resembles a narrow channel and is often referred to as an isthmus.

A focal activation point 322 is where electrical waves of excitation are initiated to propagate through the cardiac tissue 310. The focal activation point 322 could be a collection of cardiac cells. Alternatively, the focal activation point 322 could be stimulation provided by a cardiac catheter inserted into the heart. The ECG raw signal waves 326, also referred to as isochrones, radiate outwardly from the focal activation point 322. As the ECG raw signal waves 326 propagate outwardly, the ECG raw signal waves 326 are unable to penetrate the two areas of diseased tissue 314. Thus, a portion of each ECG raw signal wave 326 must travel around the areas of diseased tissue 314, along an upper branch 330 and a lower branch 334, each of the upper 330 and lower 334 branches of the signal waves 326 being referred to as a far-field component. The remaining portion of the signal wave 326 travels through the narrow channel 318, or isthmus, and is referred to a near-field component, which is the portion of the signal wave that is of primary interest to the mapping engine and the medical professionals performing the cardiac mapping.

The cardiac tissue of the narrow channel 318 is often less diseased than the diseased tissue 314 surrounding it, and is sufficiently healthy to allow the near-field component of the signal waves 326 to travel therethrough, although at a significantly slower rate than the far-field component of the signal wave 326 traveling along the upper and lower branches 330 and 334 and around the areas of diseased tissue 314. The rate of propagation of the near-field component of the signal wave 326 through the narrow channel 318 of cardiac tissue 310 is comparatively slow when compared to the rate of propagation of the far-field component of the signal wave 326 traveling along the upper and lower branches 330 and 334 around the areas of diseased tissue 314. The outward waves travel faster than the wave travelling through the isthmus as represented by crowding of the isochrones in that area. Slow propagation leads to late exit of the near-field component of the signal waves 326 from the narrow channel 318 which may induce a new (reentrant) wave because the end of refractory of the vital tissue allows re-excitation. Thus, it is crucial to detect the near-field component of the signal waves 326 as they exit the narrow channel 318.

One or more probes/catheters can be inserted within the heart and placed within the area of the narrow channel 318. The catheter may include one or multiple unipolar measuring electrodes 361, 362, and 363 arranged to be positioned within the narrow channel 318 for the purpose of measuring propagation of the near-field component of the signal waves 326 as they travel through the narrow channel 318. For example, the first unipolar measuring electrode 361 may be positioned close to the entrance end of the narrow channel 318, as defined by the direction of travel of the near-field component of the signal wave 326 propagating through the narrow channel 318. The second unipolar measuring electrode 362 may be positioned centrally within the narrow channel 318. The third unipolar measuring electrode 363 may be positioned in proximity to the exit end of the narrow channel 318, as defined by the direction of travel of the near-field component propagating therethrough.

During propagation of signal waves 326 from the focal activation point 322 across the cardiac tissue 310, the unipolar measuring electrodes 361, 362, and 363 of the multi-electrode catheter are arranged to detect electrical activity from the signal waves 326, both the near-field component, and the far-field component. One object of the invention is to separate the near-field component from the far-field component for closer analysis of the near-field component.

Figure 4:
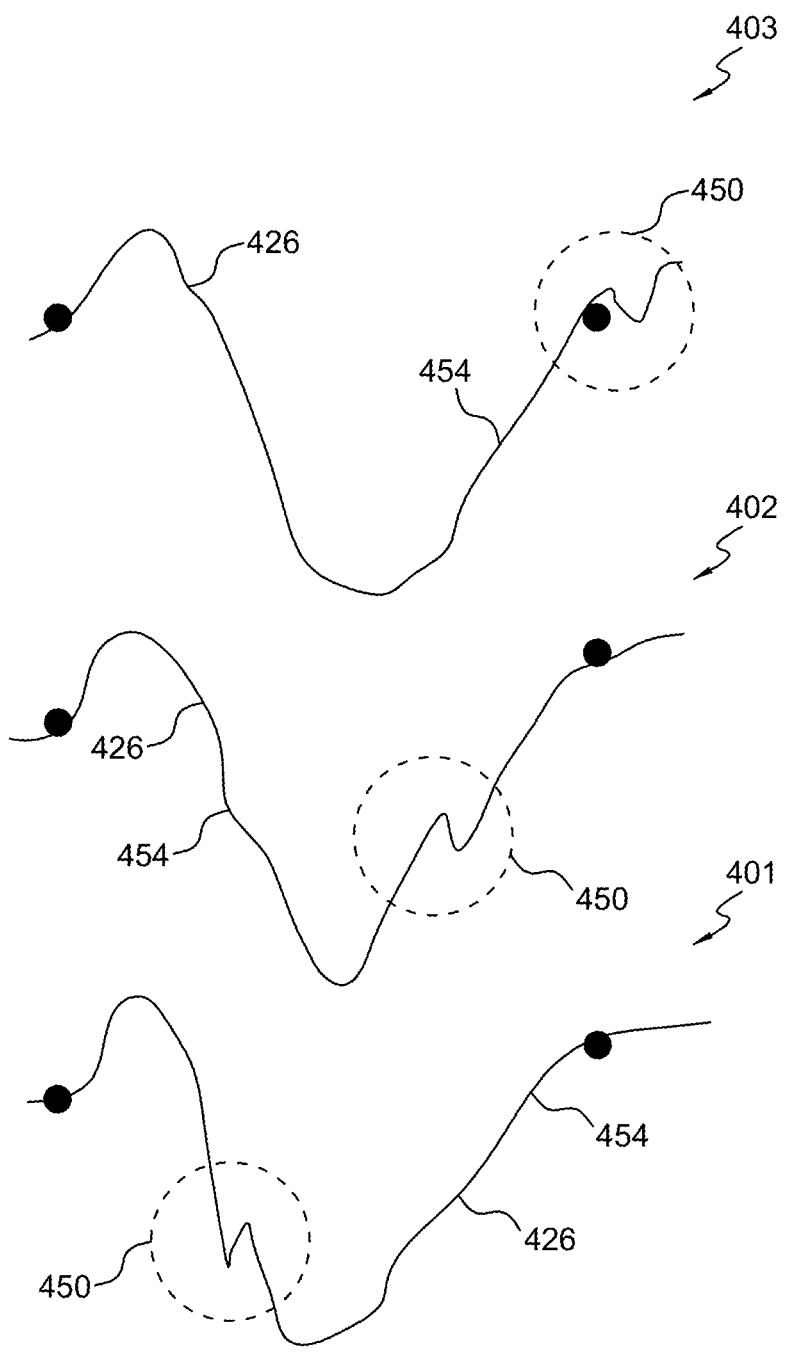
FIG. 4 depicts graphical representations according to one or more embodiments.

Referring now to FIG. 4, depicted are graphical representations 401, 402, and 403. For brevity and ease of explanation, items of FIGS. 1-3 that are supportive of the graphical representations 401, 402, and 403 are reused in the description of FIG. 4. The graphical representations 401, 402, and 403 show a single cardiac signal wave 326 propagating across the segment of cardiac tissue 310 and being detected by the unipolar measuring electrodes 361, 362, and 363 located at different positions of the cardiac tissue 310 according to one or more embodiments. That is, the graphical representations 401, 402, and 403 show a morphology (or shape) of the single cardiac signal wave 326, respectively, on the unipolar measuring electrodes 361, 362, and 363. The single cardiac signal wave 326 is represented generally in the shape more or less resembling that of a sine wave. As the single cardiac signal wave 326 travels across the narrow channel 318, it is measured at the three distinct locations within the narrow channel 318, where the three unipolar measuring electrodes 361, 362, and 363 of the multi-electrode catheter are located. In each graphical representations 401, 402, and 403, the single cardiac signal wave 326 includes a near-field component that is encircled at 450. The shape of the near-field component 450 includes a peak, which because of its comparatively small size can be designated with a lower-case r and is sometimes designated as "rS". The near-field component 450 is detected as the single cardiac signal wave 326 reaches each unipolar measuring electrode 361, 362, and 363 within the narrow channel 318. According to one or more embodiments, the near-field component 450 is illustrated as a small notch portion when compared to the overall size of the single cardiac signal wave 326. The remaining portion of the single cardiac signal wave 326 represents the far-field component 454.

The near-field component 450 is of a relatively small amplitude when compared with the far-field component 454 because there is relatively little cardiac tissue within the narrow channel 318 being activated in the vicinity of the unipolar measuring electrode. The amplitude of the signal is related to the amount of tissue being activated per unit of time, which is comparatively small within the narrow channel 318. FIGS. 1 and 2 together demonstrate that, as the near-field component 450 of the single cardiac signal wave 326 travels through the narrow channel 318, the single cardiac signal wave 326 propagates at a much slower rate than the far-field component 454. As shown in the graphical representation 401, the unipolar measuring electrode 461 of the multi-electrode catheter has already detected a significant portion of the far-field component prior to detecting the near-field component 450. In the graphical representation 402, the unipolar measuring electrode 462 has already detected a major portion of the far-field component 454 prior to detecting the near-field component 450. In the graphical representation 403, the far-field component 454 of the single cardiac signal wave 326 has almost completely passed across the unipolar measuring electrode 363 located in proximity to the exit end of the narrow channel 318 before detecting the near-field component 450. Such a delayed near-field component 450 exiting the narrow channel can lead to the creation of a reentrant circuit which can result in ventricular tachycardia. Thus, it is desirable to focus attention on the near-field component 450, by eliminating the far-field component.

Figure 5:
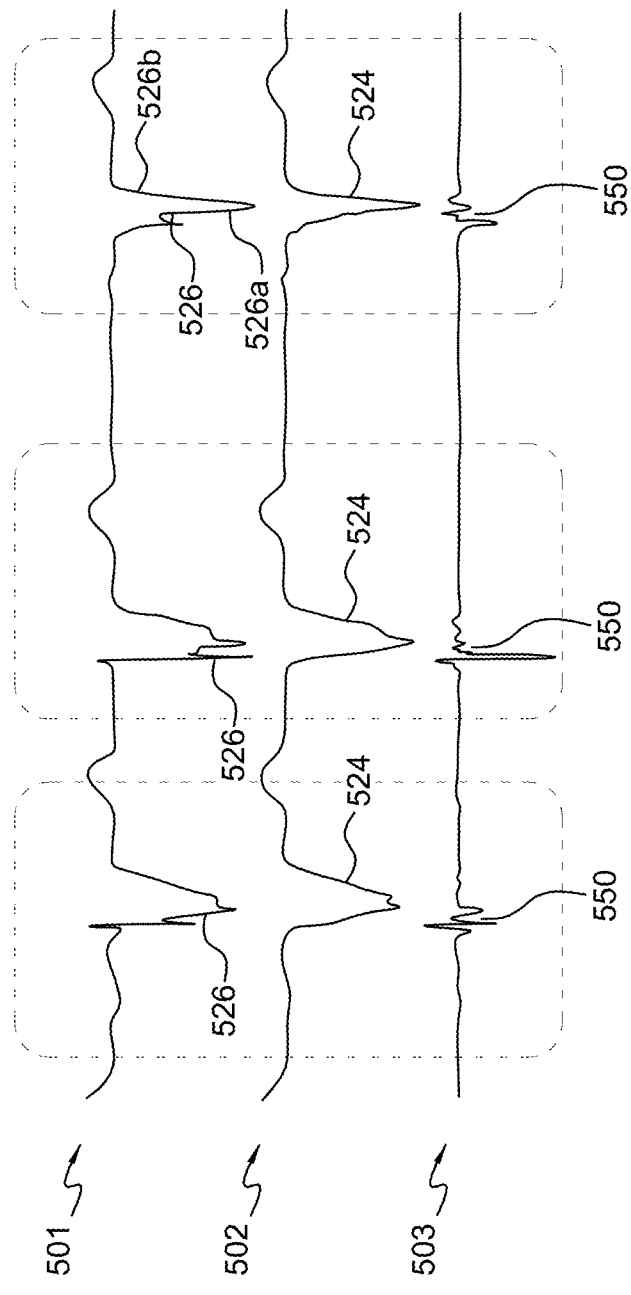
FIG. 5 depicts plots according to one or more embodiments.

Referring now to FIG. 5, plots 501, 502, and 503 are shown according to one or more embodiments. These plots 501, 502, and 503 illustrate an exemplary raw ECG signal 501 and a decomposition into constituent parts, including a far-field component 502 and a near-field component 503. Note that a voltage is plotted along the y-axis, and time is plotted along the x-axis. The exemplary raw ECG signal 501 is an example of the raw ECG single cardiac signal wave 326 detected by the unipolar measuring electrode 361 and its decomposition into its constituent parts including the far-field component 454 (e.g., far-field component 502) and the near-field component 450 (e.g., near-field component 503).

According to one or more embodiments, the mapping engine provides or decomposing the raw ECG single cardiac signal wave 326 into its far-field component 454 and the near-field component 450. As the far-field component 454 is at a comparatively greater distance from the unipolar measuring electrodes 361, 362, and 363, the rate of change over time of the far-field component 454 of the signal as detected by the electrodes is relatively slow as indicated by the relatedly smooth shape of the signal curves 524 of the plot 502 of FIG. 5. Likewise, because the near-field component 450 is at a comparatively closer distance from the unipolar measuring electrodes 361, 362, and 363, the rate of change over time of the near-field component 450 of the signal is relatively fast, as indicated by the sharper or spikier shape of the signal curves 550 of the plot 503 of FIG. 5, including the steep negative slope. Based upon the resulting shape of the raw ECG single cardiac signal wave 326, it is evident that the near-field component 450 and far-field component 454, in combination, are shown located on the downstroke 526a of the signal 526 signal of the plot 501 of FIG. 5, while the far-field component 454, alone, is shown on the upstroke 526b.

Figure 6:
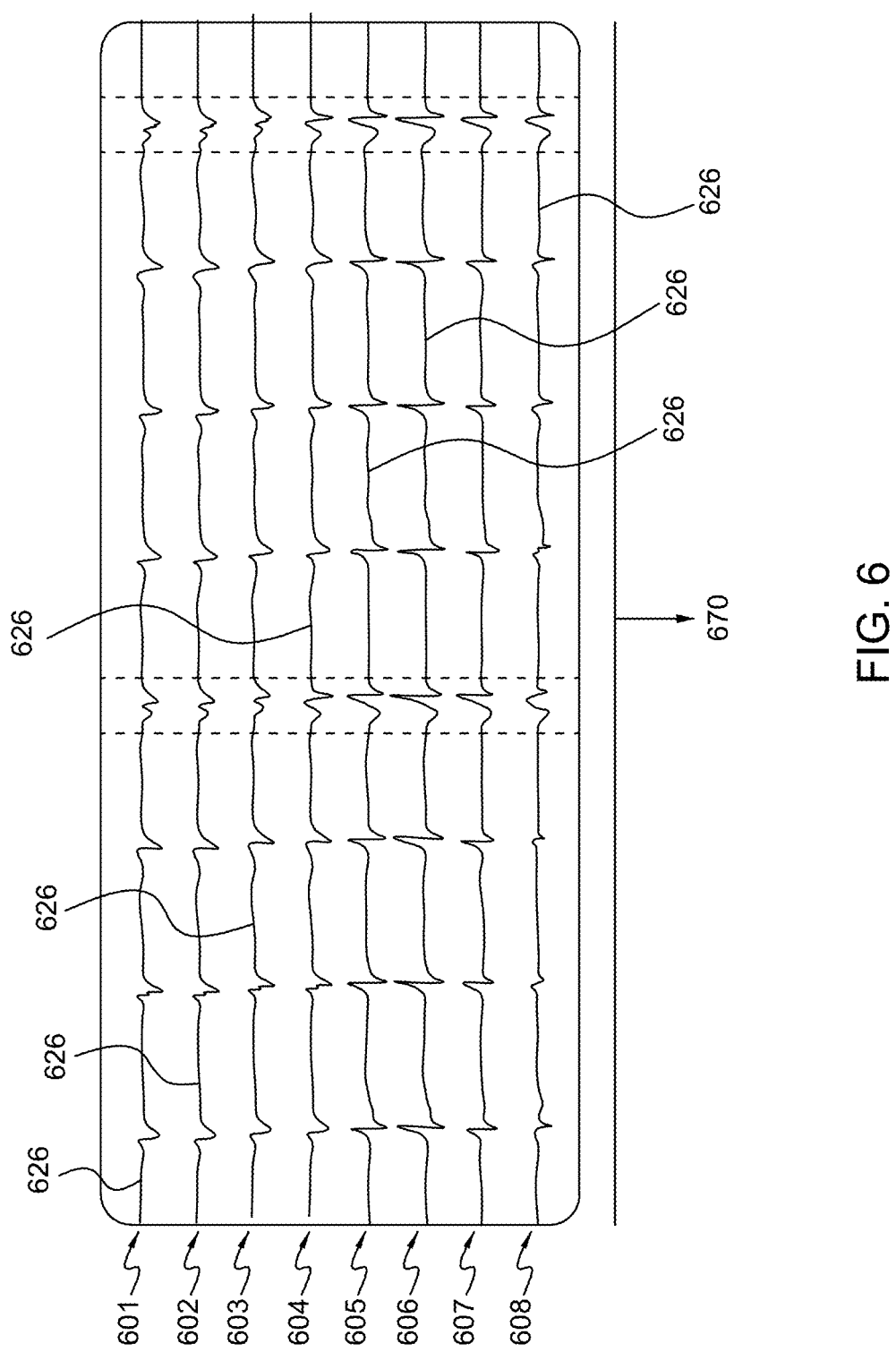
FIG. 6 depicts plots according to one or more embodiments.

According to one or more embodiments, the mapping engine determines a signal projection with respect to a spatial temporal variant. Turning to FIG. 6, plots 601, 602, 603, 604, 605, 606, 607, and 608 are shown. These plots 601, 602, 603, 604, 605, 606, 607, and 608 illustrate raw ECG signal waves 626 obtained by a plurality of measuring electrodes of a multi-electrode catheter located at different locations within cardiac tissue 310. Each of the raw ECG single cardiac signal wave 326 detected includes a near-field component 450, and a far-field component 454. For instance, a signal projection can include an ensemble mean 670, which is an initial estimate of a mean signal that is intended to be morphologically as close as possible to the far-field component 454. The ensemble mean can be developed, by the mapping engine, using an ensemble mean averaging method. An ensemble mean 670 signal can then be subtracted from the raw ECG signal waves 626, leaving the near-field component 450, which is the signal of interest.

For example, the eight raw ECG signal waves 626 illustrated in the plots 601, 602, 603, 604, 605, 606, 607, and 608 may be obtained by utilizing eight measuring electrodes of a multi-electrode catheter. Note, the number of measuring electrodes utilized is merely exemplary, and a greater or fewer number of measuring electrodes may be employed to obtain a greater or fewer number of raw ECG signal waves 626. The number of electrodes used can be dynamically changed, based on morphology of the signals, the electrode location, prior information that was received during far-field analysis of prior beats in similar position. For example, twenty measuring electrodes of a multi-electrode catheter may be utilized.

The raw ECG signal waves 626 are then averaged. Because the far-field components 454 of the raw ECG signal waves 326 being averaged are relatively distant from the unipolar measuring electrodes 361, 362, and 363 regardless of the position of the measuring electrodes within the cardiac tissue, the far-field components 454 appear to be very similar to each other in morphology (shape) and highly correlated. By contrast, because the near-field components 450 are being detected in relatively close range to the unipolar measuring electrodes 361, 362, and 363, which are placed at different positions within the cardiac tissue 310, the near-field components 450 appear to be very different from one another in morphology and not correlated. By calculating an average of the overall raw ECG signal waves 626, the component that is more or less equal in morphology from signal to signal and is highly correlated, i.e., the far-field component 454, will not be canceled during the averaging process. By contrast, the component that differs in morphology from one measuring electrode to another and is not correlated, i.e., the near-field component 450, will cancel out due to the differences in morphology from one ECG signal to the next. When the average is calculated, the near-field component 450 cancels out, leaving a reference signal having a morphology approximating the far-field component 454. Alternatively, instead of using the raw ECG signal as described above, a reduced dimensionality signal derived from the raw ECG signal may be utilized. Examples of such a projection are the use of principal component analysis (PCA), singular devalue decomposition (SVD), and/or forms of filter banks and wavelets. Once the raw ECG signal waves 626 are decomposed, the mapping engine can progress the method 100 at block 145 and form (either fully or with reduced dimensionality) the near and far-field components 450 and 454.

According to one or more embodiments, the mapping engine determines a signal projection with respect to a time variant. For example, under certain circumstances, the mapping engine may not require multiple electrodes of a multi-electrode catheter placed at different positions within the cardiac tissue for obtaining multiple raw ECG signals for calculating an ensemble mean. Thus, the mapping engine can implement a method for calculating an ensemble mean utilizing a single signal obtained from a single electrode of a catheter. That is, a single measuring electrode is utilized to detect a plurality of segments of a raw ECG single cardiac signal wave 326 during a predetermined period of time. Turning to a plot 700 of FIG. 7, each segment that is of interest is referred to as a complex 760. Typically, a baseline 762 or flat portion of the raw ECG signal 726 is not of clinical interest and is excluded from the complex 760. As cardiac beats pass under the electrode, the raw ECG signal 726 rises from the baseline 762 until it reaches a certain value, which is the peak 768, and then very quickly falls to a trough 776 and then gradually returns to baseline 762. The complex 760 is the portion of the raw ECG single cardiac signal wave 326 that is of interest.

Figure 7:
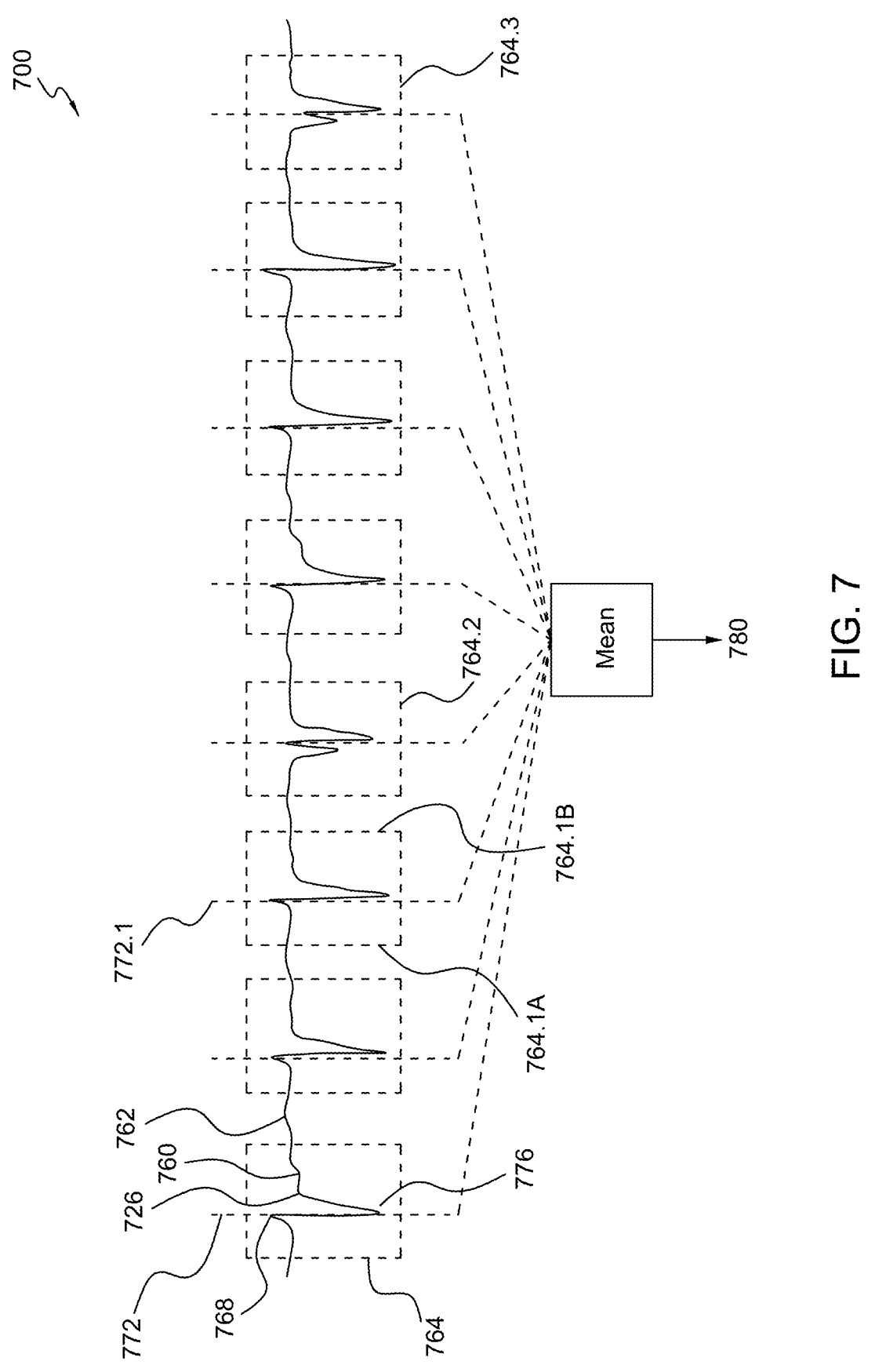
FIG. 7 depicts a plot according to one or more embodiments.

Further, as shown in FIG. 7, eight complexes 760 of a raw ECG signal 326 are detected by a single measuring electrode during a 2.5 second period of time. The raw ECG signal 326 from which the complexes 760 are obtained could be a tachycardia such as an atrial or ventricular tachycardia, or could be a normal sinus rhythm. Each complex 760 within the raw ECG signal 26 includes a peak 768, a trough 776, and other features. Each complex 760 is shown positioned within a rectangle-shaped frame 764. Each frame 764 represents an interval of time corresponding to the elapsed time for occurrence of each complex 760, e.g., approximately 150 msec. in duration. The frame 764 is utilized for the purpose of comparing and averaging the complexes 760 in determining an ensemble mean 780 under this time variant calculation. The peak 768 (or the start of the downward slope) of each complex 760 may be utilized as an anchor point or fiducial marker demarcated by a vertical line 772. Alternatively, the trough 776, or any other feature that is common to all of the complexes 760, could serve as the anchor point for marking. Since the time interval for the occurrence of each complex 760 along the raw ECG signal 326 is not necessarily constant, the anchor point may be utilized as a reference for comparing the complexes 760 to each other for determining the ensemble mean 780. In particular, once the anchor point is established and demarcated with the vertical line 772 for each complex 760, the frame 764 may be defined around the anchor point 772. For example, a first side A of the frame 764.1 can be defined by moving to a left of the vertical line 772.1 by 50 msec. Likewise, a second side B of the frame 764.1 can be defined by moving to a right of the vertical line 772.1 by 100 msec. It should be understood that these frames may be defined in other ways, e.g., other time intervals may be utilized for sizing the frame 764. For example, the complex 760 may be between 50 and 200 msec wide requiring a larger frame 764. Alternatively, defining the interval may be automated as a fraction of the beat interval, i.e., the mean interval measured between the vertical lines of the full course of the ECG signal 326. In this manner, the entire complex 760 as captured within the frame 764 may be segmented from the remainder of the raw signal 326 and averaged with the other complexes 760 to arrive at an ensemble mean 780, wherein the near-field component 450 is canceled out leaving a reference signal having a morphology approximating the far-field component 454.

According to one or more embodiments, the time variant ensemble means described herein can be applied to each of the signals discussed above in connection with the spatial temporal variant of the ensemble means to combine the two methods for calculating the ensemble means.

According to one or more embodiments, under the time variant ensemble means described above, complexes 760 that are morphologically different from or not well correlated with the remaining complexes 760 in the group may be filtered out prior to calculating the ensemble mean. For example, FIG. 7 illustrates a tachycardia occurring in the atrium wherein the first three complexes 760 of the group from the left represent atrial activations and are very much similar to each other in morphology. By contrast, the fourth complex 764.2 in the group (highlighted) differs in morphology from the first three, and may represent a ventricular activation. Likewise, a right-most complex 764.3 in FIG. 7, also highlighted, differs in morphology from the others in the group. These complexes 764.2 and 764.3, which differ morphologically, can be eliminated prior to the ensemble mean calculation. Such morphologically different complexes 764.2 and 764.3 may be identified by calculating the cross-correlation among the complexes 760 and filtering out any that are not adequately correlated with the remaining complexes 760 within the group.

Returning to the method 100 of FIG. 1, at sub-block 155, the mapping engine applies one or more filters to the reference signal and to the raw ECG signal wave. An exemplary filter for this application may be an adaptive finite impulse response (AFIR) filter. Other exemplary filters suitable for this application may include filters within a class of linear filters, such as infinite impulse response filters, and filters within a class of non-linear filters, such as median filters or morphological filters. The reference signal is filtered for further refinement.

Figure 8:
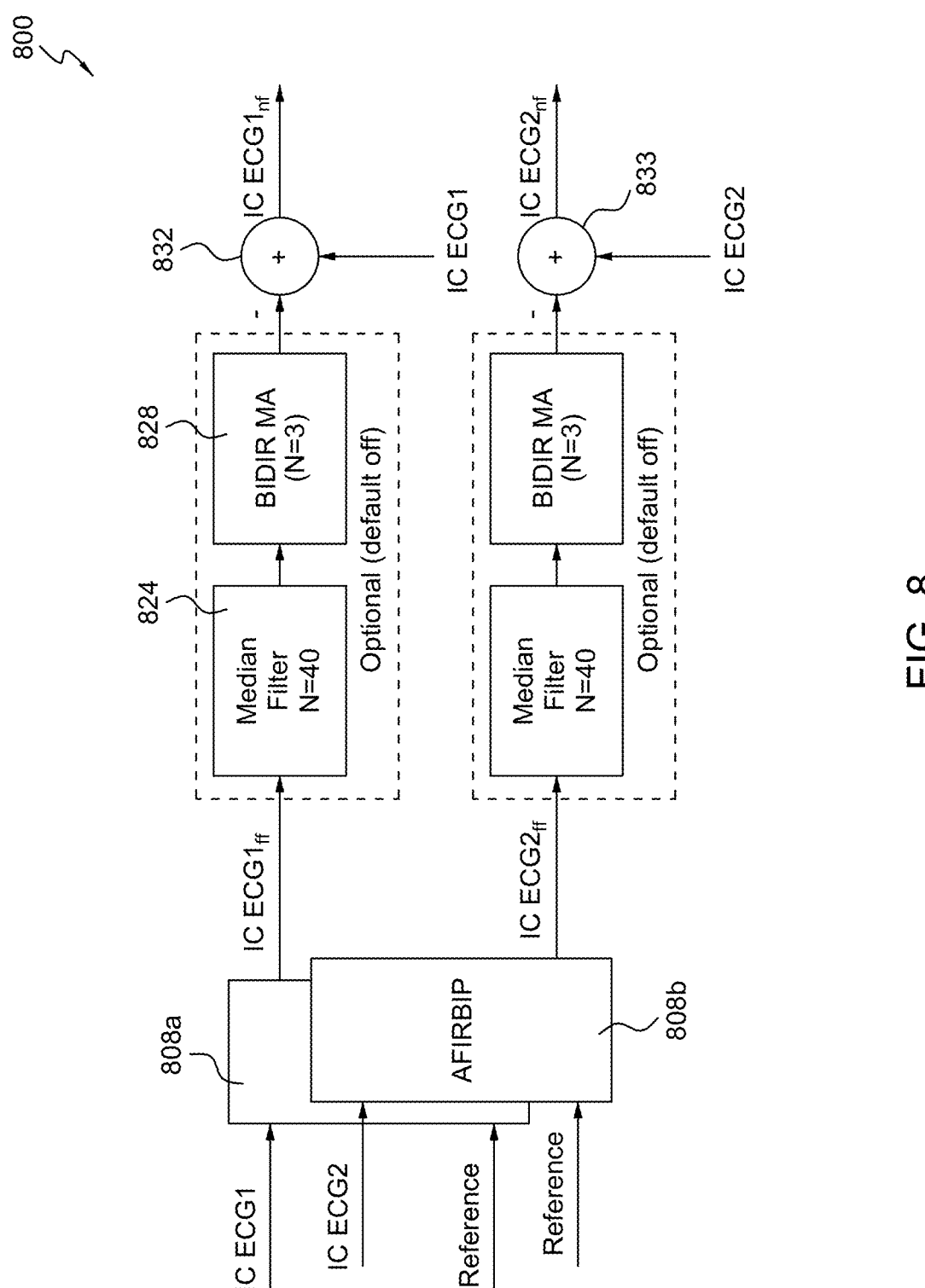
FIG. 8 depicts a diagram according to one or more embodiments.
Figure 9:
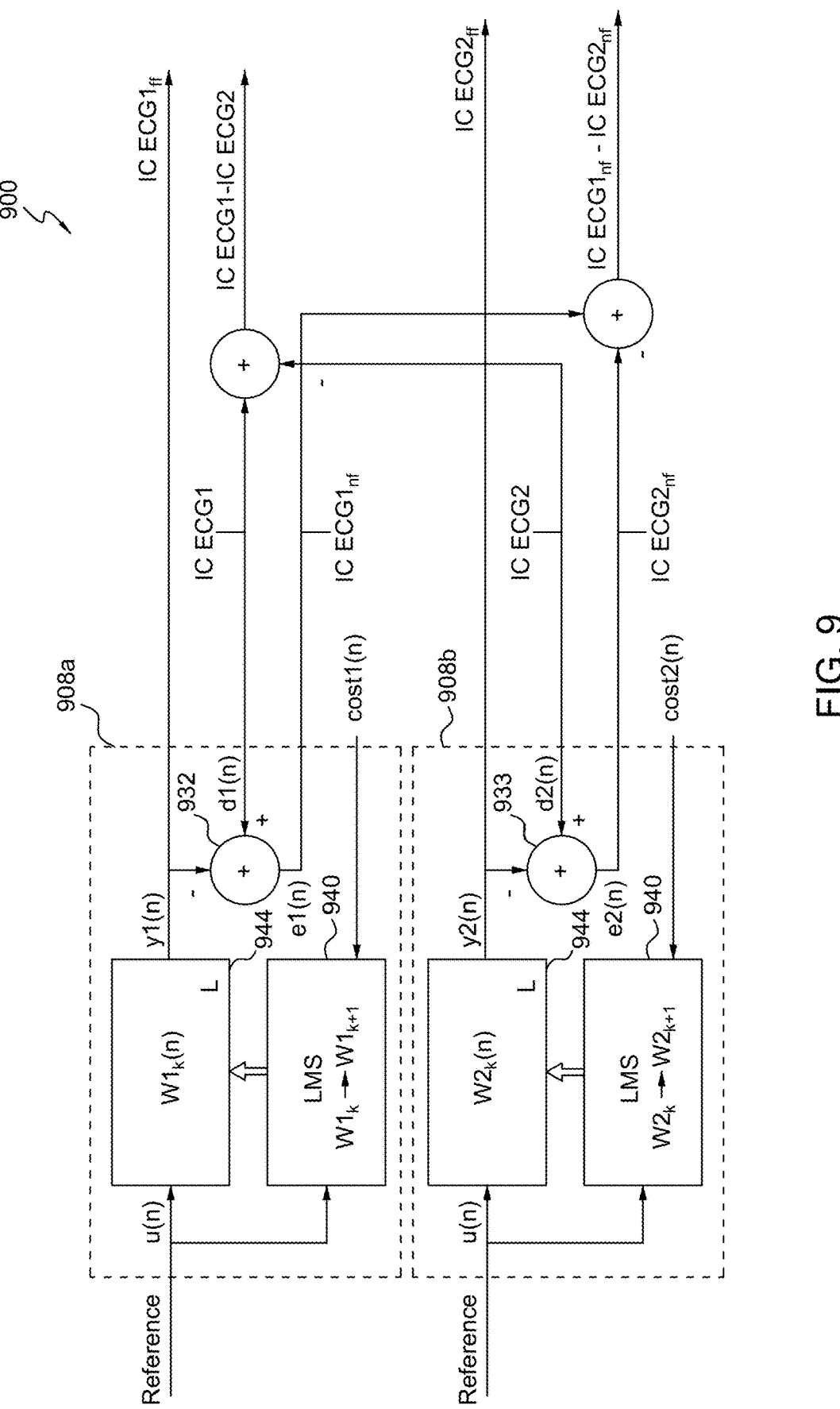
FIG. 9 depicts a diagram according to one or more embodiments.
Figure 10:
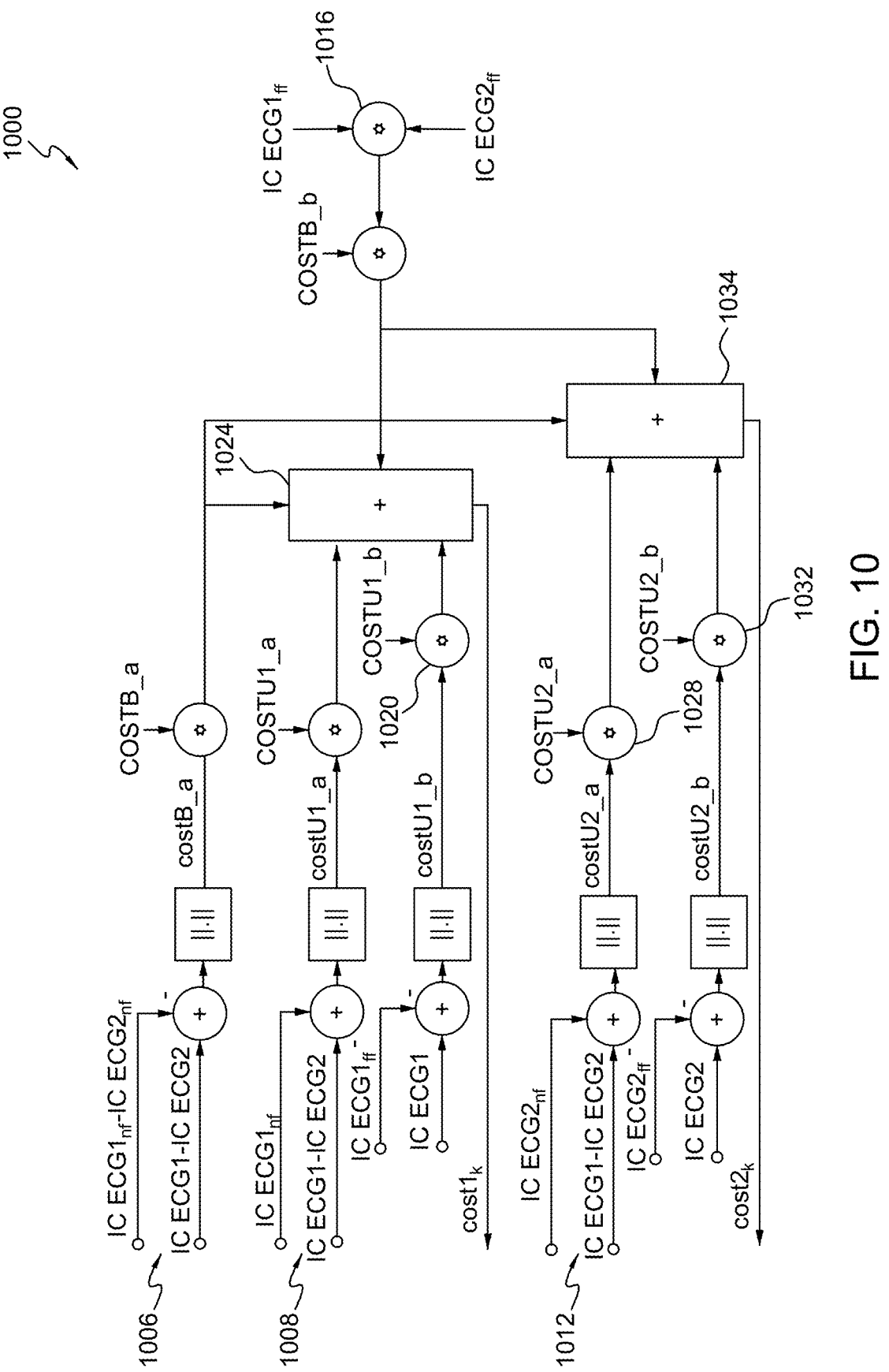
FIG. 10 is a schematic diagram illustrating a manner for determining a cost function utilized in further refining the near-field component of the IC ECG signal according to one or more embodiments.

According to one or more embodiment, the mapping engine implements sub-block 155 according to FIGS. 8-10. FIG. 8-10 respectively depict diagrams 800, 900, and 1000. The schematic diagram 1000 illustrates operations of an adaptive finite impulse response (AFIRBIP) filter structure of the mapping engine. AFIRBIP filter structure of the mapping engine refines a near-field component of the ICECG signal according to one or more embodiments.

Referring now to FIG. 800, there is shown therein a schematic diagram illustrating the use of an AFIRBIP filter structure to further refine the approximation of the far-field component 454 based upon the reference signal input. On the left-hand side of the figure, two unipolar IC ECG signals (IC ECG1 and IC ECG2) are shown which may have been recorded by two separate unipolar electrodes located in proximity to each other within the cardiac tissue as described above. The two separate unipolar signals (IC ECG1 and IC ECG2) are shown being inputted into respective adaptive finite impulse AFIRBIP filter structures indicated at 808a and 808b. (By subtracting the two unipolar signals, IC ECG1 and IC ECG2 from one another, a bipolar value may be obtained.) In addition, on the left-hand side of the figure, two reference signals (Reference) developed through one of the ensemble mean calculations described above, are shown being inputted into a respective one of the AFIRBIP filter structure 808a and 808b. Each of the reference signals has been developed and corresponds to one of the unipolar signals (IC ECG1 and IC ECG2). The resulting output of the AFIRBIP filter structure 808a and 808b is a better-tuned or an improved approximation of the far-field component, indicated at IC ECG1$_{ff}$ and IC ECG2$_{ff}$. Moving in the right-hand direction, each of these far-field components (IC ECG1$_{ff}$ and IC ECG2$_{ff}$) is then post-processed by being inputted into a median filter 824 and a bi-directional moving average filter 828. At operations 832 and 833, each respective far-field component (IC ECG1$_{ff}$ and IC ECG2$_{ff}$) is subtracted (as indicated by the minus sign) from its respective raw unipolar signal (IC ECG1 and IC ECG2) to obtain an approximation of the near-field component (IC ECG1$_{nf}$ and IC ECG2$_{nf}$) associated with each of the unipolar signals (IC ECG1 and IC ECG2). This near-field component is also depicted at 503 in FIG. 5.

A more detailed presentation of the AIFRBIP filter structures 808a and 808b is provided in the diagram 900 of FIG. 9. At the left-hand side of the diagram 900, the two reference signals, along with the two unipolar signals (IC ECG1 and IC ECG2) are shown inputted into the respective adaptive finite impulse AFIRBIP filter structures 908a and 908b, resulting in a better-tuned far-field component indicated by (IC ECG1$_{ff}$ and IC ECG2$_{ff}$). At operations 932 and 933, the estimated far-field components (IC ECG1$_{ff}$ and IC ECG2$_{ff}$) are then subtracted from their respective unipolar signals (IC ECG1 and IC ECG2) to obtain an approximation of the near-field component (IC ECG1$_{nf}$ and IC ECG2$_{nf}$). The process described in FIG. 9 provides outputs that are utilized for determining cost functions (cost1$_k$ and cost2$_k$), as described in FIG. 10. The cost functions serve to measure the degree of refinement or quality of estimation of the far-field component. As shown on the right-hand side of FIG. 9, these outputs include the estimated far-field components (IC ECG1$_{ff}$ and IC ECG2$_{ff}$), a raw bipolar value (IC ECG1–IC ECG2), and a bipolar near-field component estimation (IC ECG1$_{nf}$–IC ECG2$_{nf}$). As shown in FIG. 9, the cost functions calculated in FIG. 10, are utilized in FIG. 9 to adapt or adjust filter weight factors (W1$_k$(n) and LMS) indicated at blocks 940 and 944 to obtain a more refined estimate of the far-field component (IC ECG1$_{ff}$ and IC ECG2$_{ff}$).

Referring now to FIG. 10, there is provided a schematic diagram 1000 describing the manner for measuring the value of the cost function utilizing the outputs from FIG. 9, and other inputs. The AFIRBIT filter structures 908a and 908b undergo an iterative process to optimize the value of the far-field component of the IC ECG signals, i.e., the (IC ECG1$_{ff}$ and IC ECG2$_{ff}$) which may then be subtracted from its respective raw unipolar signal (IC ECG1 and IC ECG2) to obtain an approximation of the near-field component (IC ECG1$_{nf}$ and IC ECG2$_{nf}$).

As shown in FIG. 10, a cost value (cost1$_k$) is calculated with respect to the first IC ECG signal (IC ECG1) based upon inputs obtained from FIG. 9, and other inputs; and a cost value (cost2$_k$) is calculated with respect to the second IC ECG signal (IC ECG2) based upon the inputs obtained from FIG. 9, and other inputs. At first, the value of the cost function (cost1$_k$ and cost 2$_k$) may be undesirably high. These cost values may then be carried back to the AFIRBIT filter structures 908a and 908b at block 944 (FIG. 9), where adjustments may be made to the coefficient of the filter weight factors (W1k(n) and LMS) indicated at blocks 940 and 944 to obtain a more refined estimate of the far-field component (IC ECG1ff and IC ECG2ff). As a result of these adjustments, new values for the outputs shown in FIG. 9 may be obtained which may then be utilized for calculating new values of the cost function (cost1k and cost 2k) as shown in FIG. 10. As iterations continue, subsequent values for the cost function (cost1k and cost 2k) may continue to decrease based upon adjustment to the filter weight factors until the value of the cost functions (cost1k and cost 2k) reaches a predetermined minimum threshold, also referred to as an error surface. Once the error surface or minimum has been reached, the iterative process may stop yielding an optimized IC ECG far-field component value, which may be subtracted from the raw unipolar signal to obtain an optimized IC ECG near-field value.

Continuing on FIG. 10, the figure is broken down into four branches: a bipolar branch indicated at 1006, an upper unipolar branch indicated at 1008, a lower unipolar branch indicated at 1012, and a far-field branch indicated at 1016. At the start of the bipolar branch 806, the raw signals are subtracted from one another (IC ECG1–IC ECG2) to obtain a raw bipolar value. The near-field component of the IC ECG signals may then be subtracted from each other (IC ECG1$_{nf}$–IC ECG2$_{nf}$) to obtain a difference which may then subtracted from the raw bipolar value. The absolute value of this difference is a cost value costB_a. The cost value costB_a may then be multiplied by a weight factor (between 0 and 1) to obtain a weighted cost indicated at COSTB_a relating to the bipolar signal. A weight factor of zero indicates that the cost value would have no effect in the summation block discussed below. A weight factor of greater value will result in a cost value having greater influence in the summation block, discussed below.

At the far-field branch 1016, far-field field components of the signals are subtracted from one another (IC ECG1$_{ff}$–IC ECG2$_{ff}$) and the difference may then be multiplied by a weight factor, e.g., between 0 and 1, to obtain a weighted cost indicated at COSTB_b.

For the upper unipolar branch 1008, the IC ECG2 raw signal may be subtracted from the IC ECG1 raw signal to obtain a bipolar value. That value may then be subtracted from the IC ECG1$_{nf}$ component value. The absolute value of that difference is represented as costU1_a. At operation 1016, the costU1_a value may be multiplied by a weight factor (e.g., between 0 and 1) to obtain a weighted cost indicated at COSTU1_a. Also, of interest is how far the IC ECG1$_{ff}$ far-field component is deviating from IC ECG1 signal. Thus, the far-field component IC ECG1$_{ff}$ may be subtracted from the IC ECG1 signal to obtain a difference, the absolute value of which is the cost costU1_b. At operation 1020, the costU1_b value may be multiplied by a weight factor, e.g., between 0 and 1, to obtain a weighted cost indicated at COSTU1_b. At operation 1024, the COSTU1_a and COSTU1_b values associated with the upper unipolar branch may be summed in the summation block along with the raw bipolar value COSTB_a, and the far-field value COSTB-b to arrive at cost1$_k$.

Similarly, for the lower unipolar branch 1012, the IC ECG2 raw signal may be subtracted from the IC ECG1 raw signal to obtain a bipolar value. That value may then be subtracted from the IC ECG2$_{nf}$ near-field component value. The absolute value of that difference is represented as costU2_a. At operation 1028, the costU2_a value may be multiplied by a weight factor (e.g., between 0 and 1) to obtain a weighted cost indicated at COSTU2_a. Also, of interest is how far the IC ECG2$_{ff}$ far-field component is deviating from IC ECG2 signal. Thus, the far-field component IC ECG2$_{ff}$ may be subtracted from the IC ECG2 signal to obtain a difference, the absolute value of which is costU2_b. At operation 1032, the costU2_b value may be multiplied by a weight factor, e.g., between 0 and 1, to obtain a weighted cost indicated at COSTU2_b. At step 1034, the COSTU2_a and the COSTU2_b values associated with the lower unipolar branch may be summed at the summation block along with the raw bipolar value COSTB_a and the far-field value COSTB_b to arrive at cost2$_k$. In total, there are six weight factors employed, COSTB_a, COSTU1_a, COSTU1_b, COSTU2_a, COSTU2_b, and COSTB_b.

Referring back to FIG. 9, the cost1$_k$ and cost2$_k$ values obtained from FIG. 10, as described above, are utilized as inputs at cost1(n) and cost2(n) to the W1$_k$(n) and LMS blocks at 940 and 944. Utilizing these cost inputs, the W1$_k$(n) and LMS blocks generate a new set of weight factors to be applied for determining new cost values as discussed in FIG. 10. With the weight factors properly readjusted at each iteration, the cost values (cost1$_k$ and cost2$_k$) continue to decrease until the cost values (cost1$_k$ and cost 2$_k$) reach a predetermined minimum threshold, also referred to as an error surface. Cost can be associated with specific morphology of the ventricle activity (such as polymorphic VT). If several activities exist, their sources may be different and the projection of the far-field would be different leading to different optimal cost. Once the error surface or minimum has been reached, the iterative process may stop yielding an optimized IC ECG far-field component value which may be subtracted from the raw IC ECG signal to obtain an optimized near field signal. In addition to the foregoing, other algorithms are applied for the purpose of minimizing the cost values (cost1$_k$ and cost 2$_k$). For example, such algorithms may include RLS, LXP, normalized LMS, LMS-Newton etc. When cost is high, or when the estimate leads to the conclusion that far-field is not reduced sufficiently, this can be used as an indication not to annotate based on these specific beats.

Returning to the method 100 of FIG. 1, at sub-block 160, the mapping engine isolates/removes/discards the further-refined reference signal (i.e., far-field component) from the raw ECG signals to generate a near-field signal that is substantially free of the far-field component.

At block 180, the mapping engine utilizes the near-field components for localizing in time where a wave went under at least one of the plurality of electrodes. According to one or more embodiments, the mapping engine generates one or more signal values localizing in time the near-field components. These signal values can be provided as inputs to one or more algorithms of the mapping engine (e.g., to understanding conduction patterns and deviation thereof), to the mapping engine for a visualization of the physiological signals, etc. In this regard, for example, the mapping engine can provide the inputs, as filtered signals, to the one or more annotation algorithms to extract additional signals. The mapping engine can also provide the input to one or more computer algorithms that further determine and analyze local activity. The mapping engine can further communicatively couple to an output device to output the processed near-field component, such as on a display. Alternatively, the signal wave may include only a far-field component, such as in scar tissue. Thus, the method 100 of the mapping engine provides the technical effect, advantage, and benefit of signal interpretation of the ECG/ICEG in support of fundamentally understanding the electrical conduction system of the heart, as normal conduction starts and propagates in a predictable pattern, and deviation from this pattern can be a normal variation or be pathological.

Figure 11:
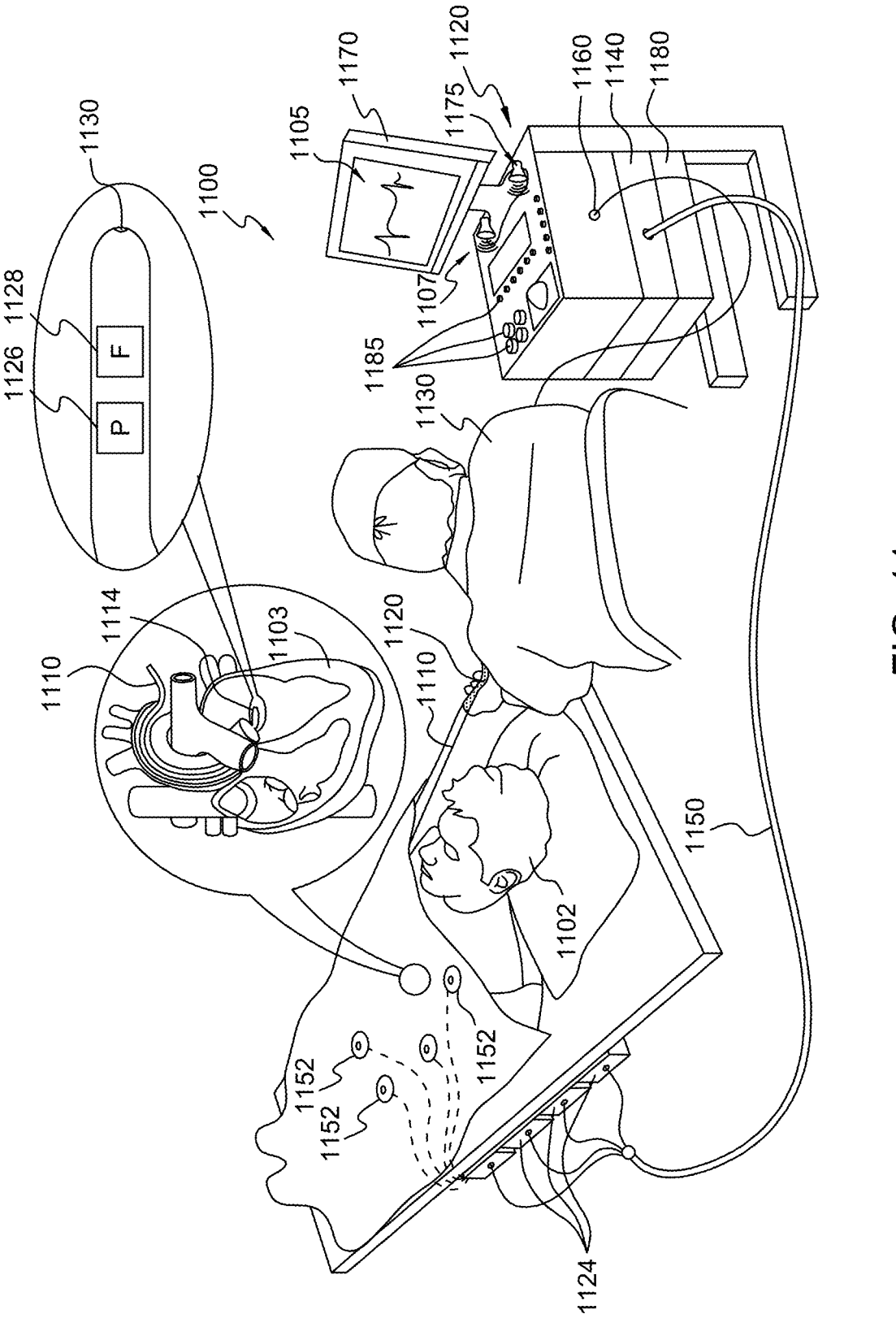
FIG. 11 is a high-level illustration of an example medical system for improving annotation of ventricle activity during a medical procedure such as a mapping procedure according to one or more embodiments.

FIG. 11 is a high-level illustration of an example medical system 1100 for improving annotation of ventricle activity during a medical procedure such as a mapping procedure, and to control the deployment of various probes within a subject. Example system 1100 includes a probe 1110, such as an intracardiac catheter, a console 1120 and an associated probe control unit 1112. As described herein, it will be understood that probe 1110 is used for diagnostic or therapeutic treatment, such as for example, mapping electrical potentials in a heart 1103 of a patient 1102 or performing an ablation procedure. Alternatively, probe 1110 can be used, mutatis mutandis, for other therapeutic and/or diagnostic purposes in heart 1103, lungs, or in other body organs and ear, nose, and throat (ENT) procedures.

An operator 1130 can, for example, insert probe 1110 into the vascular system of patient 1102 using probe control unit 1112 so that a distal end 1114 of probe 1110 enters a chamber of the patient's heart 1103. Console 1120 can use magnetic position sensing to determine position coordinates of distal end 1114 inside heart 1103. To determine the position coordinates, a driver circuit 1122 in console 1120 may drive field generators 1124 to generate magnetic fields within the body of patient 1102. Field generators 1124 can include coils that may be placed below the torso of the patient 1103 at known positions external to patient 1102. These coils may generate magnetic fields in a predefined working volume that contains heart 1103.

A location sensor 1126 within distal end 1114 of probe 1110 can generate electrical signals in response to these magnetic fields. A signal processor 1140 can process these signals in order to determine the position coordinates of distal end 1114, including both location and orientation coordinates. Known methods of position sensing described hereinabove are implemented in the CARTO™ mapping system produced by Biosense Webster Inc., of Diamond Bar, Calif., and is described in detail in the patents and the patent applications cited herein.

Location sensor 1126 is configured to transmit a signal to console 1120 that is indicative of the location coordinates of distal end 1114. Location sensor 1126 can include one or more miniature coils, and typically can include multiple coils oriented along different axes. Alternatively, location sensor 1126 can include either another type of magnetic sensor, or position transducers of other types, such as impedance-based or ultrasonic location sensors.

Probe 1110 can also include a force sensor 1128 contained within distal end 1114. Force sensor 1128 can measure a force applied by distal end 1114 to the endocardial tissue of heart 1103 and generate a signal that is sent to console 1120. Force sensor 1128 can include a magnetic field transmitter and a receiver connected by a spring in distal end 1114, and can generate an indication of the force based on measuring a deflection of the spring. Further details of this type of probe and force sensor are described in U.S. Patent Application Publications 2009/0093806 and 2009/0138007, and are incorporated herein by reference as if fully set forth. Alternatively, distal end 1114 can include another type of force sensor that can use, for example, fiber optics or impedance measurements.

Probe 1110 can include an electrode 1130 coupled to distal end 1114 and configured to function as an impedance-based position transducer Additionally or alternatively, electrode 1130 can be configured to measure a certain physiological property, for example the local surface electrical potential of the cardiac tissue at one or more of the multiple locations. Electrode 1130 can be configured to apply radio frequency (RF) energy to ablate endocardial tissue in heart 1103.

Although example medical system 1100 can be configured to measure the position of distal end 1114 using magnetic-based sensors, other position tracking techniques can be used (e.g., impedance-based sensors). Magnetic position tracking techniques are described, for example, in U.S. Pat. Nos. 5,391,199, 5,443,489, 6,788,967, 6,690,963, 5,558,091, 6,172,499, and 6,177,792, and are incorporated herein by reference as if fully set forth. Impedance-based position tracking techniques are described, for example, in U.S. Pat. Nos. 5,983,126, 6,456,864 and 5,944,022, and are incorporated herein by reference as if fully set forth.

Signal processor 1140 can be included in a general-purpose computer, with a suitable front end and interface circuits for receiving signals from probe 1110 and controlling the other components of console 1120. Signal processor 1140 can be programmed, using software, to carry out the functions that are described herein. The software can be downloaded to console 1120 in electronic form, over a network, for example, or it can be provided on non-transitory tangible media, such as optical, magnetic or electronic memory media. Alternatively, some or all of the functions of signal processor 1140 can be performed by dedicated or programmable digital hardware components.

In the example of FIG. 11, console 1120 can also be connected by a cable 1150 to external sensors 1152. External sensors 1152 can include body surface electrodes and/or position sensors that can be attached to the patient's skin using, for example, adhesive patches. The body surface electrodes can detect electrical impulses generated by the polarization and depolarization of cardiac tissue. The position sensors can use advanced catheter location and/or magnetic location sensors to locate probe 1110 during use. Although not shown in FIG. 11, external sensors 1152 can be embedded in a vest that worn by patient 1102. External sensors 1152 can aid in identifying and tracking the respiration cycle of patient 1103. External sensors 1152 can transmit information to console 1120 via cable 1150.

Additionally, or alternatively, probe 1110, and external sensors 1152 can communicate with console 1120 and one another via a wireless interface. For example, U.S. Pat. No. 6,266,551, whose disclosure is incorporated herein by reference, describes, inter alia, a wireless catheter, which is not physically connected to signal processing and/or computing apparatus. Rather, a transmitter/receiver is attached to the proximal end of the catheter. The transmitter/receiver communicates with a signal processing and/or computer apparatus using wireless communication methods, such as infrared (IR), radio frequency (RF), wireless, Bluetooth®, acoustic or other transmissions.

Probe 1110 can be equipped with a wireless digital interface that can communicate with a corresponding input/output (I/O) interface 1160 in console 1120. Wireless digital interface and the I/O interface 1160 can operate in accordance with any suitable wireless communication standard that is known in the art, such as IR, RF, Bluetooth, one of the IEEE 802.11 families of standards, or the HiperLAN standard. External sensors 1152 can include one or more wireless sensor nodes integrated on a flexible substrate. The one or more wireless sensor nodes can include a wireless transmit/receive unit (WTRU) enabling local digital signal processing, a radio link, and a power supply such as miniaturized rechargeable battery.

Wireless digital interface and the I/O interface 1160 can enable console 1120 to interact with probe 1110 and external sensors 1152. Based on the electrical impulses received from external sensors 1152 and signals received from probe 1110 via Wireless digital interface and the I/O interface 1160 and other components of medical system 1100, signal processor 1140 can generate information 1105 which can be shown on a display 1170.

Figure 12:
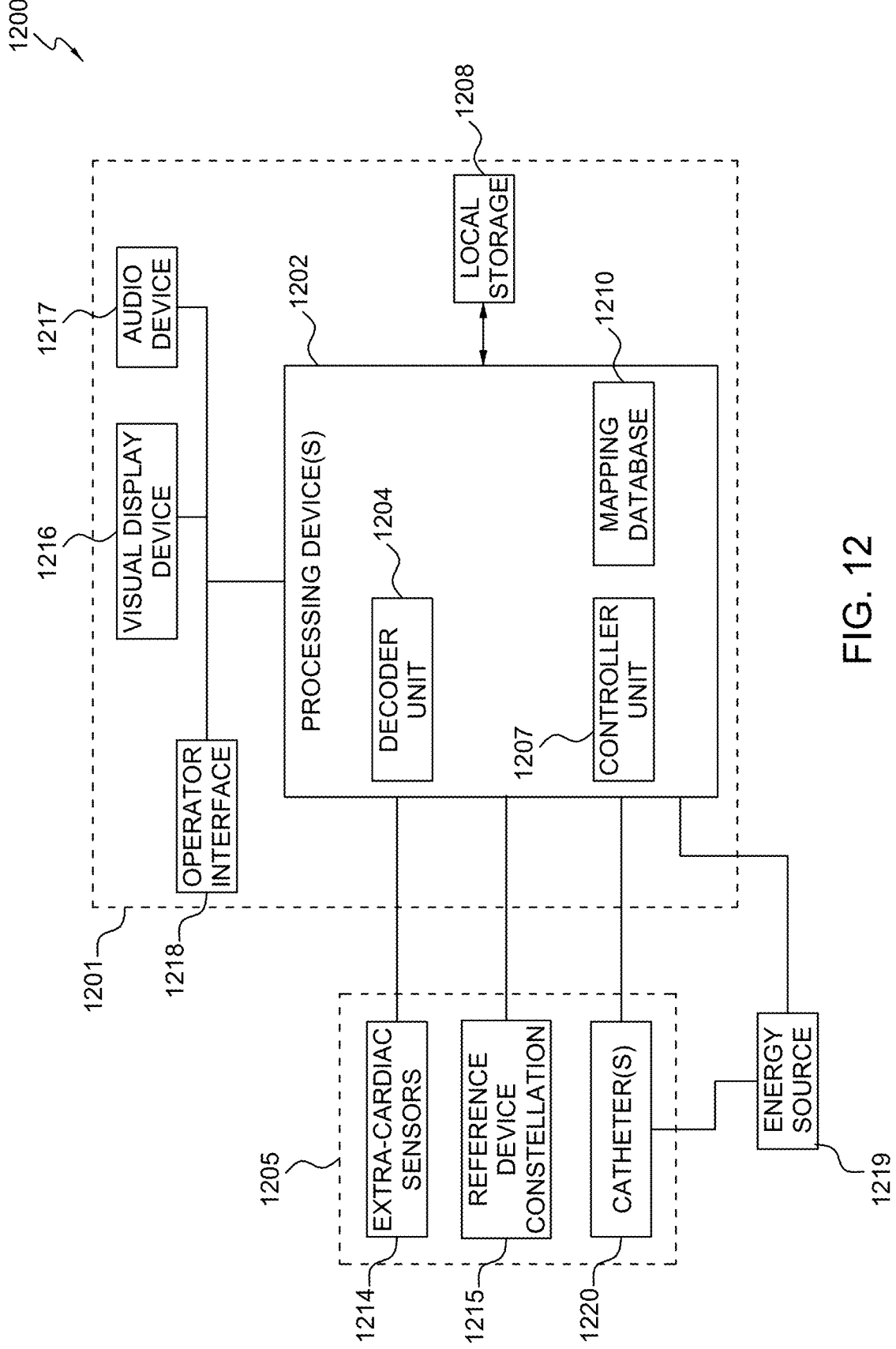
FIG. 12 is a detailed schematic diagram of an example medical system in accordance with certain implementations according to one or more embodiments.

FIG. 12 is a more detailed schematic diagram of an example medical system 1200, which may include features for improving annotation of ventricle activity during a medical procedure. Medical system 1200, which may be for illustration purposes, a cardiac mapping and ablation system, may include, but is not limited to, any of the following components: a console system 1201; extra-cardiac sensors 1214; reference device constellation 1215; energy source 1219; and/or catheter(s) 1220.

Operator interface(s) 1218 may be used by one or more operators to interact with and control medical system 1200. Operator interface(s) 1218 may include, but are not limited to include, the following devices: a keyboard; a touch-sensitive display; and/or a mouse. Operator interface(s) 1218 may allow operators to access and manipulate visual information, and may provide them with the ability to change views, and tag and/or label lesions to keep track of treatment strategies for individual patients. Operators of medical system 1200 may include, but are not limited to include, the following: a physician (e.g., an electrophysiologist) who may, for example, control the catheter, gather and interpret diagnostics, and perform the ablation procedure; and a Clinical Application Specialist (CAS) who functions as the physician's assistant during the procedures.

Reference device constellation 1215 (e.g., may be referred to as a location pad) may include a ring of computer-controlled (e.g., controlled by processing device(s) 1202) magnets positioned beneath the patient 1205. The magnets may have known and fixed strength and position values that may be used as point of origin references for the magnetic fields in the surrounding space and may provide the reference information to processing device(s) 1202 to be used in producing accurate 3D images of the heart.

Extra-cardiac sensor(s) 1214 may be electrodes on the skin of a patient 1205, for example. Extra-cardiac sensor(s) 1214 may detect the electrical activity of the heart via detection of electrical changes on the skin due to the electro-physiologic pattern of the heart, and provide information on the electrical activity to processing device(s) 1202 to be used in diagnosing arrhythmias and determining a therapeutic course of action. Processed versions of the extra-cardiac signals detected by extra-cardiac sensor(s) 1214 may be displayed on visual display device 1216, for example in a graphical user interface (GUI).

One or more devices may be used on patient 1205 for therapeutic and diagnostic purposes. In example medical system 1200, catheter(s) 1220 are shown and as described herein for these purposes; however, other devices may be used for diagnostics and/or therapeutic treatment. When the catheter(s) 1220 is used for performing ablation on a target location (e.g., one or more locations along a path), for example by applying RF energy, catheter(s) 1220 may receive the RF energy from energy source 1219, as may be instructed by processing device(s) 1202. In an example, catheter(s) 1220 may request the RF energy directly from energy source 1219.

According to one or more embodiments, a medical system for removing far-field components from raw unipolar electrical signals is provided herein. The medical system includes a cardiac catheter that includes a plurality of electrodes disposed thereon. The plurality of electrodes positioned at locations within cardiac tissue apart from one another and the captures raw unipolar electrical signals transmitted through the cardiac tissue. Each of the raw unipolar electrical signals including a near-field component and a far-field component. The medical system includes a processing device communicatively coupled to the catheter. The processing device processes the captured raw unipolar electrical signals by receiving the captured raw unipolar electrical signals from the plurality of electrodes, calculating an ensemble mean of the captured raw unipolar electrical signals to generate a reference signal that estimates the morphology of the far-field component, applying a filter to the reference signal and to the raw unipolar electrical signals to generate a further-refined reference signal that is an improved estimate of the morphology of the far-field component, and subtracting the further-refined reference signal from the raw unipolar electrical signals to generate a processed near-field signal that is substantially free of the far-field component. The medical system includes a display device to output the processed near-field component.

According to one or more embodiments or any of the medical system embodiments herein, the medical system can include a median filter. The processing device can apply the median filter to the further-refined reference signal prior to subtracting the further-refined reference signal from the raw unipolar electrical signals.

According to one or more embodiments or any of the medical system embodiments herein, the medical system can include a bidirectional moving average filter. The processing device applies the bidirectional moving average filter to the further-refined reference signal prior to subtracting the further-refined reference signal from the raw unipolar electrical signals.

According to one or more embodiments or any of the medical system embodiments herein, the plurality of electrodes can include two or more electrodes.

According to one or more embodiments or any of the medical system embodiments herein, the catheter can include a plurality of unipolar electrodes positioned in pairs, with each pair spaced approximately 2 mm apart from each other.

According to one or more embodiments or any of the medical system embodiments herein, the plurality of unipolar electrodes can include 20 unipolar electrodes arranged in 10 pairs.

According to one or more embodiments or any of the medical system embodiments herein, the filter can include at least one of an adaptive finite impulse response filter, an infinite impulse response filter, a linear filter, a non-linear filter, and a morphological filter.

According to one or more embodiments or any of the medical system embodiments herein, the filter can include filter weights. The processing device processes the captured raw unipolar electrical signals by utilizing a cost function to measure a degree of refinement of the further-refined reference signal, and adjusting the filter weights based upon the value of the cost function to optimize the further-refined reference signal.

According to one or more embodiments, a medical system for removing far-field components from raw unipolar electrical signals is provided herein. The medical system includes a cardiac catheter that includes a single electrode disposed thereon, the single electrode positioned at a location within cardiac tissue and that captures a raw electrical signal that includes a plurality of cardiac complexes. Each cardiac complex of the plurality of cardiac complexes includes a near-field component, and a far-field component. The plurality of complexes are captured sequentially over a predetermined period of time. The medical system includes a processing device communicatively coupled to the catheter. The processing device processes the plurality of cardiac complexes by receiving the captured plurality of cardiac complexes from the single electrode, calculating an ensemble mean by averaging the plurality of cardiac complexes to generate a reference signal that approximates the morphology of the far-field component, applying a filter to the reference signal and to the raw unipolar electrical signal to generate a further-refined reference signal that is an improved estimate of the morphology of the far-field component, and subtracting the further-refined reference signal from the raw unipolar electrical signal to generate a processed near-field signal that is substantially free of the far-field component. The medical system includes a display device to output the processed near-field component.

According to one or more embodiments or any of the medical system embodiments herein, the processing device can calculate a correlation threshold among the captured plurality of cardiac complexes, compare the morphology of each cardiac complex with the correlation threshold, and eliminate from the plurality of cardiac complexes any cardiac complex having a morphology that does not meet or exceed the correlation threshold.

According to one or more embodiments or any of the medical system embodiments herein, the processing device can average the plurality of cardiac complexes by selecting a fiducial feature common to each cardiac complex in the plurality of cardiac complexes, aligning the fiducial feature in each cardiac complex of the plurality of cardiac complexes, and comparing the morphologies of the plurality of cardiac complexes.

According to one or more embodiments or any of the medical system embodiments herein, the fiducial feature can be at least one of a peak, a trough, and a maximum slope portion of each cardiac complex.

According to one or more embodiments or any of the medical system embodiments herein, the adaptive finite impulse response filter additionally can include filter weights. The processing device can utilize a cost function to measure a degree of refinement of the further-refined reference signal and adjust the filter weights based upon the value of the cost function to optimize the further-refined reference signal.

According to one or more embodiments or any of the medical system embodiments herein, the capturing the raw electrical signal can include a plurality of cardiac complexes is carried out during normal sinus rhythm.

According to one or more embodiments or any of the medical system embodiments herein, the capturing the raw electrical signal can include a plurality of cardiac complexes is carried out during atrial or ventricular arrhythmia.

According to one or more embodiments or any of the medical system embodiments herein, the filter can include at least one of an adaptive finite impulse response filter, an infinite impulse response filter, a linear filter, a non-linear filter, and a morphological filter.

According to one or more embodiments, a method for removing far-field components from raw unipolar electrical signals is provided herein. The method includes utilizing a cardiac catheter comprising a plurality of electrodes disposed thereon. The plurality of electrodes are positioned at locations within cardiac tissue apart from one another to capture raw unipolar electrical signals transmitted through the cardiac tissue. Each of the raw unipolar electrical signals include a near-field component and a far-field component. The method includes processing the captured raw unipolar electrical signals by receiving the captured raw unipolar electrical signals from the plurality of electrodes, calculating an ensemble mean of the captured raw unipolar electrical signals to generate a reference signal that estimates the morphology of the far-field component, applying a filter to the reference signal and to the raw unipolar electrical signals to generate a further-refined reference signal that is an improved estimate of the morphology of the far-field component, and subtracting the further-refined reference signal from the raw unipolar electrical signals to generate a processed near-field signal that is substantially free of the far-field component. The method includes outputting the processed near-field component to a display device.

According to one or more embodiments or any of the method embodiments herein, the method can include applying a median filter to the further-refined reference signal prior to subtracting the further-refined reference signal.

According to one or more embodiments or any of the method embodiments herein, the method can include applying a bidirectional moving average filter to the further-refined reference signal prior to subtracting the further-refined reference signal. According to one or more embodiments or any of the method embodiments herein, the method filter can include filter weights.

According to one or more embodiments or any of the method embodiments herein, the method can include utilizing a cost function to measure a degree of refinement of the further-refined reference signal, and adjusting the filter weights based upon the value of the cost function to optimize the further-refined reference signal.

According to one or more embodiments or any of the method embodiments herein, the filter can include at least one of an adaptive finite impulse response filter, an infinite impulse response filter, a linear filter, a non-linear filter, and a morphological filter.

According to one or more embodiments, a medical system is provided. The medical system includes a processing device communicatively coupled to one or more probes. The processing device operates to cause the medical system perform receiving physiological signals from a plurality of electrodes of the one or more probes; decomposing the physiological signals into near-field component and far-field component by using mutual information from a set of the plurality of electrodes; and utilizing the near-field components for localizing in time where a wave went under at least one of the plurality of electrodes.

According to one or more embodiments or any of the medical system embodiments herein, the processing device can generate one or more signal values localizing in time the near-field components and provides the one or more signal values as inputs to one or more algorithms or for a visualization.

According to one or more embodiments or any of the medical system embodiments herein, the mutual information can include electrical activity occurring throughout a heart chamber that commonly received by each electrode of the plurality of electrodes.

According to one or more embodiments or any of the medical system embodiments herein, the far-field components can include the electrical activity detected by each electrode of the plurality of electrodes at distances on an order of centimeters.

According to one or more embodiments or any of the medical system embodiments herein, the near-field components can include electrical activity detected by each electrode of the plurality of electrodes at distances on an order of millimeters.

According to one or more embodiments or any of the medical system embodiments herein, the one or more probes can include a cardiac catheter.

According to one or more embodiments or any of the medical system embodiments herein, the plurality of electrodes of the catheter can comprise a plurality of unipolar electrodes positioned in pairs, with each pair spaced approximately 1 millimeter or 2 millimeter apart from each other.

According to one or more embodiments or any of the medical system embodiments herein, the plurality of unipolar electrodes can include at least three unipolar electrodes arranged in any configuration of pairs.

According to one or more embodiments or any of the medical system embodiments herein, the plurality of electrodes can be positioned at locations within cardiac tissue apart from one another and configured to the physiological signals transmitted through the cardiac tissue.

According to one or more embodiments or any of the medical system embodiments herein, the processing device can generate one or more signal values localizing in time the near-field components and can provide the one or more signal values to a display device for a visualization.

According to one or more embodiments, a method is provided. The method is implemented by a processing device communicatively coupled to one or more probes. The method includes receiving physiological signals from a plurality of electrodes of the one or more probes; decomposing the physiological signals into near-field component and far-field component by using mutual information from a set of the plurality of electrodes; and utilizing the near-field components for localizing in time where a wave went under at least one of the plurality of electrodes.

According to one or more embodiments or any of the method embodiments herein, the processing device can generate one or more signal values localizing in time the near-field components and provides the one or more signal values as inputs to one or more algorithms or for a visualization.

According to one or more embodiments or any of the method embodiments herein, the mutual information can include electrical activity occurring throughout a heart chamber that commonly received by each electrode of the plurality of electrodes.

According to one or more embodiments or any of the method embodiments herein, the far-field components can include the electrical activity detected by each electrode of the plurality of electrodes at distances on an order of centimeters.

According to one or more embodiments or any of the method embodiments herein, the near-field components can include electrical activity detected by each electrode of the plurality of electrodes at distances on an order of millimeters.

According to one or more embodiments or any of the method embodiments herein, the one or more probes can include a cardiac catheter.

According to one or more embodiments or any of the method embodiments herein, the plurality of electrodes of the catheter can comprise a plurality of unipolar electrodes positioned in pairs, with each pair spaced approximately 1 millimeter or 2 millimeter apart from each other.

According to one or more embodiments or any of the method embodiments herein, the plurality of unipolar electrodes can include at least three unipolar electrodes arranged in any configuration of pairs.

According to one or more embodiments or any of the method embodiments herein, the plurality of electrodes can be positioned at locations within cardiac tissue apart from one another and configured to the physiological signals transmitted through the cardiac tissue.

According to one or more embodiments or any of the method embodiments herein, the processing device can generate one or more signal values localizing in time the near-field components and can provide the one or more signal values to a display device for a visualization.

As indicated herein, embodiments disclosed herein may include apparatuses, systems, methods, and/or computer program products at any possible technical detail level of integration. The computer program product may include a computer readable storage medium (or media) having computer readable program instructions thereon for causing a controller to carry out aspects of the present invention.

The computer readable storage medium can be a tangible device that can retain and store computer readable program instructions. The computer readable storage medium may be, for example, but is not limited to, an electronic storage device, a magnetic storage device, an optical storage device, an electromagnetic storage device, a semiconductor storage device, or any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

The computer readable program instructions described herein can be communicated and/or downloaded to respective controllers from an apparatus, device, computer, or external storage via a connection, for example, in-band communication. Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

The flowchart and block diagrams in the drawings illustrate the architecture, functionality, and operation of possible implementations of apparatuses, systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the flowchart and block diagrams in the drawings. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used herein, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A medical system for generating an intracardiac electrogram (ICEG) of a heart of a patient that improves cardiac mapping, the medical system comprising:
   one or more probes that measure one or more physiological parameters of the heart of the patient; and
   one or more processors that are communicatively coupled to the one or more probes, wherein the one or more processors are collectively configured to:
   receive physiological signals from a plurality of electrodes of the one or more probes,
   derive a reduced dimensionality signal from the physiological signals,
   decompose the physiological signals into a near-field component and a far-field component based on the reduced dimensionality signal,
   utilize the near-field component to localize a point in time where a wave went under at least one of the plurality of electrodes,
   form a recomposed near-field component and a recomposed far-field component by fully recomposing the near-field component and the far-field component to full dimensionality, and
   generate the ICEG for the heart of the patient, wherein the ICEG is calculated based on the recomposed near-field component, the recomposed far-field component and the point in time.

2. The medical system of claim 1, wherein:
   the physiological signals are further decomposed into the near-field component and the far-field component based on mutual information, and
   the mutual information comprises electrical activity occurring throughout a heart chamber that is commonly received by each electrode of the plurality of electrodes.

3. He medical system of claim 2, wherein the far-field component comprise the electrical activity detected by each electrode of the plurality of electrodes at distances on an order of centimeters.

4. The medical system of claim 1, wherein the near-field component comprise electrical activity detected by each electrode of the plurality of electrodes at distances on an order of millimeters.

5. The medical system of claim 1, wherein the one or more probes comprises a cardiac catheter.

6. The medical system of claim 5, wherein the plurality of electrodes of the cardiac catheter comprises a plurality of unipolar electrodes that are positioned in pairs, with each pair spaced approximately 1 millimeter or 2 millimeter apart from adjacent pairs.

7. The medical system of claim 6, wherein the plurality of unipolar electrodes comprises at least three unipolar electrodes arranged in any configuration of pairs.

8. The medical system of claim 1, wherein the plurality of electrodes are positioned at locations within cardiac tissue apart from one another and configured to detect the physiological signals transmitted through the cardiac tissue.

9. The medical system of claim 1, wherein the one or more processors are further collectively configured to:
   store the ICEG for the heart of the patient in a memory, and
   provide the ICEG for the heart of the patient to a display device for a visualization.

10. A method for generating an intracardiac electrogram (ICEG) of a heart of a patient that improves cardiac mapping, the method comprising:

receiving physiological signals from a plurality of electrodes of one or more probes, wherein the one or more probes measure one or more physiological parameters of the heart of the patient;

deriving a reduced dimensionality signal from the physiological signals;

decomposing the physiological signals into a near-field component and a far-field component based on the reduced dimensionality signal;

utilizing the near-field component to localize a point in time where a wave went under at least one of the plurality of electrodes;

forming a recomposed near-field component and a recomposed far-field component by fully recomposing the near-field component and the far-field component to full dimensionality; and generating the ICEG for the heart of the patient, wherein the ICEG is calculated based on the recomposed near-field component, the recomposed far-field component and the point in time.

11. The method of claim 10, wherein:

the physiological signals are further decomposed into the near-field component and the far-field component based on mutual information, and the mutual information comprises electrical activity occurring throughout a heart chamber that commonly received by each electrode of the plurality of electrodes.

12. The method of claim 11, wherein the far-field component comprise the electrical activity detected by each electrode of the plurality of electrodes at distances on an order of centimeters.

13. The method of claim 10, wherein the near-field component comprise electrical activity detected by each electrode of the plurality of electrodes at distances on an order of millimeters.

14. The method of claim 10, wherein the one or more probes comprises a cardiac catheter.

15. The method of claim 14, wherein the plurality of electrodes of the cardiac catheter comprises a plurality of unipolar electrodes that are positioned in pairs, with each pair spaced approximately 1 millimeter or 2 millimeter apart from adjacent pairs.

16. The method of claim 15, wherein the plurality of unipolar electrodes comprises at least three unipolar electrodes arranged in any configuration of pairs.

17. The method of claim 10, wherein the plurality of electrodes are positioned at locations within cardiac tissue apart from one another and configured to the physiological signals transmitted through the cardiac tissue.

18. The method of claim 10, the method further comprising:

storing the ICEG for the heart of the patient in a memory; and providing the ICEG for the heart of the patient to a display device for a visualization.

19. The medical system of claim 1, wherein the reduced dimensionality signal is derived using at least one of principal component analysis (PCA) or singular devalue decomposition (SVD).

20. The method of claim 10, wherein the reduced dimensionality signal is derived using at least one of principal component analysis (PCA) or singular devalue decomposition (SVD).

* * * * *